(12) United States Patent
Howard et al.

(10) Patent No.: US 8,808,743 B2
(45) Date of Patent: *Aug. 19, 2014

(54) BENZONATATE COMPOSITIONS AND METHODS OF USE

(71) Applicants: William Wayne Howard, Morristown, NJ (US); Russell Francis Somma, Sparta, NJ (US)

(72) Inventors: William Wayne Howard, Morristown, NJ (US); Russell Francis Somma, Sparta, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/713,089

(22) Filed: Dec. 13, 2012

(65) Prior Publication Data

US 2013/0096191 A1 Apr. 18, 2013

Related U.S. Application Data

(63) Continuation-in-part of application No. 12/925,353, filed on Oct. 20, 2010, now Pat. No. 8,357,398.

(51) Int. Cl.
| | |
|---|---|
| *A61K 9/14* | (2006.01) |
| *A61K 9/20* | (2006.01) |
| *A61K 9/54* | (2006.01) |
| *A61K 31/075* | (2006.01) |
| *A61K 31/245* | (2006.01) |
| *B01J 45/00* | (2006.01) |

(52) U.S. Cl.
USPC ........... 424/483; 424/465; 424/501; 514/538; 514/544; 514/716; 514/717; 514/718; 521/30

(58) Field of Classification Search
None
See application file for complete search history.

(56) References Cited

U.S. PATENT DOCUMENTS 6,569,463 B2 * 5/2003 Patel et al. .................. 424/497

OTHER PUBLICATIONS

US Pharmacopeia Benzonatate [online] retrieved on Apr. 9, 2013 from: http://www.pharmacopeia.cn/v29240/usp29nf24s0_m8250.html; 2 pages.*
Rohm and Hass Amberlite IRP64; Feb. 2005; 5 pages.*

* cited by examiner

*Primary Examiner* — Ernst Arnold
(74) *Attorney, Agent, or Firm* — Sheldon Kavesh

(57) ABSTRACT

Benzonatate resinates of weak acid ion exchange resins having the same distribution of butyl 4-aminobenzoate homologs as exist in the benzonatate listed in the F.D.A. Orange Book as Application No. N011210. These resinates, in simulated gastrointestinal dissolution, release essentially the same distribution of butyl-4 aminobenzoate homologs as exist in the benzonatate listed in the F.D.A. Orange Book as Application No. N011210.

29 Claims, 10 Drawing Sheets

FIGURE 3

FORMOSA LABORATORIES, INC.
36, Hoping Street, Louchu County,
Taoyuan, Taiwan, 338
Tel : 886-3-3240895    Fax : 886-3-3240923
Internet : www.formosalab.com    E-mail : info@formosalab.com

Certificate of Analysis

| Product: Benzonatate | | CAS No.: 104-31-4 |
|---|---|---|
| | | Molecular weight: 603.00 (av.) |
| Lot No.: F10510001 | Amount: 615.92 kg | MFG date: Feb. 08, 2010 |
| | | Retest date: Feb. 08, 2012 |

| | Test | Specification | Results |
|---|---|---|---|
| 1 | Appearance | Clear, pale yellow, viscous liquid | Clear, pale yellow, viscous liquid |
| 2 | Identification | | |
| | a. IR | Conforms to standard | Conforms to standard |
| | b. UV | Conforms to standard | Conforms to standard |
| 3 | UV Absorption at 420 nm | NMT 0.3 | 0.2 |
| 4 | Refractive index | 1.509~1.511 at 20° | 1.509 |
| 5 | Water | NMT 0.3 % | 0.1% |
| 6 | Residue on ignition | NMT 0.1 % | 0.0% |
| 7 | Chloride | NMT 0.0035 % | < 0.0035% |
| 8 | Sulfate | NMT 0.04 % | < 0.04% |
| 9 | Heavy metals | NMT 10 ppm | < 10 ppm |
| 10 | MPEG by TLC | NMT 0.70 % | Not detected |
| 11 | Assay | 95.0 % ~ 105.0 % | 99.0% |
| 12 | Residual Solvent (GC) | | |
| | a. Toluene | NMT 890 ppm | 23 ppm |
| 13. | Related Substances by HPLC | | |
| | a. Impurity 1: p-n-Butylaminobenzoic acid | NMT 0.15 % | 0.01% |
| | b. Impurity 2: Polyethyleneglycol-p-n-butylaminobenzoate | NMT 0.65 % | 0.10% |
| | c. Impurity 3: Ethyl-p-n-butylamino-benzoate | NMT 0.15 % | 0.02% |
| | d. Impurity 4: Polyethyleneglycol-bis-p-n-butylaminobenzoate | NMT 1.05 % | 0.05% |
| | e. Other impurity with its PA% ≥ 0.10% | Report the PA% and RRT | Not detected |
| | f. Total impurities | NMT 1.55 % | 0.20% |
| 14 | Oligomers ratio (HPLC) | | |
| | n = 3 | NMT 2 % | 0% |
| | n = 4 | NMT 4 % | 2% |
| | n = 5 | 2 % ~ 6 % | 4% |
| | n = 6 | 5 % ~ 12 % | 8% |
| | n = 7 | 9 % ~ 17 % | 12% |
| | n = 8 | 10 % ~ 20 % | 15% |
| | n = 9 | 10 % ~ 20 % | 15% |
| | n = 10 | 9 % ~ 17 % | 14% |
| | n = 11 | 7 % ~ 13 % | 11% |
| | n = 12 | 5 % ~ 9 % | 8% |
| | n = 13 | NMT 6 % | 5% |
| | n = 14 | NMT 4 % | 3% |
| | n = 15 | NMT 2 % | 2% |
| | n = 16 | NMT 2 % | 1% |
| | n = 17 | NMT 1 % | 0% |

Storage condition: Stored at or below 27°C, protected from light

Testing method: F105.E6.TS

QC Approved by: *Cloud Chang*    Date: Mar. 26, 2010

QA Approved by: *Judith Hsu*    Date: Mar. 26, 2010

BENZONATATE COMPOSITIONS AND METHODS OF USE

CROSS-REFERENCE TO RELATED APPLICATIONS

This application is a Continuation-In-Part of application Ser. No. 12/825,353 filed Oct. 20, 2010. The disclosures of that application are herein incorporated by reference to the extent not incompatible herewith.

BACKGROUND OF THE INVENTION

1. Field of the Invention

The invention relates to oral dosage forms of benzonatate useful for a tussive and anti-tussive/combination applications.

2. Description of the Related Art

Benzonatate is a non-narcotic oral antitussive (cough suppressant) drug that works by anesthetizing the tissues of the lungs and pleura responsible for the cough reflex. Benzonatate is chemically related to anesthetic agents of the para-aminobenzoic acid class (e.g., procaine; tetracaine). Benzonatate anesthetizes the stretch receptors in the respiratory passages, reducing the cough reflex. As a non-narcotic with little or no abuse potential, benzonatate is a useful drug for treating cough. Further, benzonatate does not have many of the serious side effects that narcotic cough compounds such as codeine and hydrocodone have which include:
  Narcotic Side Effects
  Overdose, respiratory depression
  Drug interactions
    Alcohol, minor tranquilizers, other CNS drugs
  Constipation, sedation
  Abuse/dependence
  Psycho/motor effects Due to these side effects, many patients cannot take narcotic cough products:
  Pain patients, abuse history, elderly, young children, COPD patients, critically ill, military/police/fire/health transportation workers, pregnant & post-partum women In spite of the many reasons to use non-narcotic cough preparations, current formulations of benzonatate have a serious safety issue that can offset its benefits as a non-narcotic alternative to codeine and hydrocodone. Current formulations of benzonatate, if released in the mouth through dissolution, either by contact with saliva or aided by chewing or sucking, can rapidly cause oropharyngeal anesthesia that may lead to adverse events including choking.

Benzonatate has a secondary pharmacologic effect as a local anesthetic. If the drug is released in the oral cavity serious adverse effects can occur. In the TESSALON™ prescription drug label, the Signs and Symptoms section states:
  "If capsules are chewed or dissolved in the mouth, oropharyngeal anesthesia will develop rapidly. CNS stimulation may cause restlessness and tremors which may proceed to clonic convulsions followed by profound CNS depression".

The formulations of the invention preserve the advantages of benzonatate while eliminating or diminishing hazards of its use. The inventive formulations of benzonatate use ion exchange resin technology to diminish or eliminate the choking hazard and adverse events if the product is released in the oral mucosa. It is believed that the use of ion exchange resins to create benzonatate compositions that can reduce or eliminate the choking and adverse effects associated with current formulations of benzonatate has not been previously disclosed. A review of the ion exchange literature and patents revealed the following pharmaceutical uses of ion-exchange resins:
  Reduce Food Effects on Pharmacokinetic Release Rates
  Taste Masking
  Disintegrant/Superdisintegrant
  Improved Dissolution
  Powder Processing Aid
  Drug Stabilization
  Oral modified release formulations: Sustained Release, Controlled Release No patent or reference source reviewed mentioned the use of ion-exchange for preventing release of a drug in the oral cavity. No patent or reference explicitly or inherently disclosed ion-exchange resinates of benzonatate. Further, no source revealed the use of denatonium benzoate or similar noxious tasting agent to prevent patients from chewing or sucking a benzonatate capsule or tablet.

It had previously been found by the inventors that benzonatate can be resinated with both a strong acid resin and a weak acid resin at significant loadings, and that, surprisingly and unexpectedly, such resinates show substantially reduced buccal dissolution rates compared to neat benzonatate. More surprisingly and yet more unexpectedly, it has now been found that only a particular class of ion exchange resins can accurately load and unload all of the molecular species found in pharmaceutical grade benzonatate.

The Merck Index, 14$^{th}$ Ed., 2006 lists benzonatate (Merck No. 1096, CAS No. [104-31-4]) as a single compound having the formula $C_4H_9-NH-C_6H_4-COO-(C_2H_4O)_9-CH_3$. However, pharmaceutical grade benzonatate, for example, TESSALON™, is a mixture of butyl 4-aminobenzoate compounds having the general formula $C_4H_9-NH-C_6H_4-COO-(C_2H_4O)_n-CH_3$, and the structure shown below and in FIG. 1.

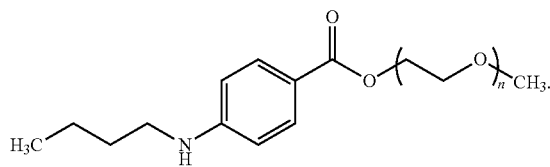

The quantity n is the number of ethoxy units in a compound of this mixture. The quantity n is typically in the range of from 3 to about 17.

SUMMARY OF THE INVENTION

The term "benzonatate" as used herein will be understood to mean a mixture of butyl 4-aminobenzoate compounds having the structure shown in FIG. 1 meeting the identification and physical test specifications of USP 28. The term "homolog" as used herein will be understood to mean a particular butyl 4-aminobenzoate compound having a specific number of ethoxy units.

It is an object of this invention to provide compositions and oral dosage forms of resinate-bound benzonatate that minimize the release of benzonatate in the oral cavity and thereby to minimize or eliminate the choking hazard associated with neat benzonatate. It is a further object of this invention to provide compositions and oral dosage forms that release the constituent homologs of resinate-bound benzonatate into a human body in essentially the same proportions as existed in the original mixture of benzonatate homologs before resination. The inventive compositions provide an answer to a problem of long standing although the implementing arts had long been available.

In a first embodiment, the invention is a resinate composition of matter comprising a mixture of individual butyl 4-aminobenzoate compounds having the formula $C_4H_9$—NH—$C_6H_4$—COO—$(C_2H_4O)_n$—$CH_3$ and the structure shown in FIG. 1; wherein the quantity n in the formula and in FIG. 1 is the number of ethoxy units in a butyl 4-aminobenzoate compound of the mixture, said quantity n having a value in the range of from at least 1 to about 25; and wherein each said compound is bound to an insoluble, weakly acid, hydrogen form cation exchange resin in the form of a resinate.

In a second embodiment, the invention is a resinate composition of matter comprising a mixture of individual butyl 4-aminobenzoate compounds having the formula $C_4H_9$—NH—$C_6H_4$—COO—$(C_2H_4O)_n$—$CH_3$ and the structure shown in FIG. 1; wherein the quantity n in the formula and in FIG. 1 is the number of ethoxy units in a butyl 4-aminobenzoate compound of the mixture, said quantity n having a value in the range of from at least 1 to about 25;

wherein each said compound is bound to an insoluble, weakly acid, hydrogen form cation exchange resin in the form of a resinate; and wherein on a resin free basis, the weight of a bound butyl 4-aminobenzoate compound divided by the total weight of bound butyl 4-aminobenzoate compounds being defined as the bound weight fraction of said compound, a regression of the number of ethoxy units in said compounds against a normal distribution of said bound weight fractions yields an index of determination, $R^2$, of at least about 0.90, a confidence level less than about 0.1, said weight fractions having a peak in the range of from about 6 to about 12 ethoxy units.

In a third embodiment, the invention is a resinate composition of matter comprising a mixture of individual butyl 4-aminobenzoate compounds having the formula $C_4H_9$—NH—$C_6H_4$—COO—$(C_2H_4O)_n$—$CH_3$ and the structure shown in FIG. 1;

wherein the quantity n in the formula and in FIG. 1 is the number of ethoxy units in a butyl 4-aminobenzoate compound of the mixture, said quantity n having a value in the range of from at least 1 to about 25;

wherein each said compound is bound to an insoluble, weakly acid, hydrogen form cation exchange resin in the form of a resinate; and wherein on a resin free basis, the weight of a bound butyl 4-aminobenzoate compound divided by the total weight of bound butyl 4-aminobenzoate compounds being defined as the bound weight fraction of said compound, said bound weight fractions when regressed against the weight fractions of the same compounds in the U.S. Food and Drug administration approved prescription drug benzonatate, said benzonatate listed in the F.D.A. Orange Book as Application No. N011210, said regression yields an index of determination, $R^2$, of at least about 0.90 and confidence level less than about 0.1

In a fourth embodiment, the invention is a resinate composition of matter comprising a mixture of individual butyl 4-aminobenzoate compounds having the formula $C_4H_9$—NH—$C_6H_4$—COO—$(C_2H_4O)_n$—$CH_3$ and the structure shown in FIG. 1;

wherein the quantity n in the formula and in FIG. 1 is the number of ethoxy units in a butyl 4-aminobenzoate compound of the mixture, said quantity n having a value in the range of from at least 1 to about 25;

wherein each said compound is bound to an insoluble, weakly acid, hydrogen form cation exchange resin in the form of a resinate; and wherein said composition is capable of release of said bound butyl 4-aminobenzoate compounds from said resinate in simulated gastrointestinal dissolution, the weight of each said released compound divided by the total weight of released compounds being defined as the released weight fraction of said compounds, said released weight fractions when regressed against the weight fractions of the same compound in the U.S. Food and Drug administration approved prescription drug benzonatate, said benzonatate listed in the F.D.A. Orange Book as Application No. N011210, said regression yields an index of determination, $R^2$, of at least about 0.90, and a significance level less than about 0.1.

In a fifth embodiment, the invention is a resinate composition of matter comprising a mixture of individual butyl 4-aminobenzoate compounds having the formula $C_4H_9$—NH—$C_6H_4$—COO—$(C_2H_4O)_n$—$CH_3$ and the structure shown in FIG. 1;

wherein the quantity n in the formula and in FIG. 1 is the number of ethoxy units in a butyl 4-aminobenzoate compound of the mixture, said quantity n having a value in the range of from at least 1 to about 25;

wherein each said compound is bound to an insoluble, weakly acid, hydrogen form cation exchange resin in the form of a resinate; and wherein on a resin free basis, the weight of a bound butyl 4-aminobenzoate compound divided by the total weight of bound butyl 4-aminobenzoate compounds being defined as the bound weight fraction of said compound, said bound weight fractions when regressed against the weight fractions of the same compounds in the mixture of free butyl 4-aminobenzoate compounds from which the resinate composition was made, said regression yields an index of determination, $R^2$, of at least about 0.90 and confidence level less than about 0.1.

In a sixth embodiment, the invention is a resinate composition of matter comprising a mixture of individual butyl 4-aminobenzoate compounds having the formula $C_4H_9$—NH—$C_6H_4$—COO—$(C_2H_4O)_n$—CH; and the structure shown in FIG. 1;

wherein the quantity n in the formula and in FIG. 1 is the number of ethoxy units in a butyl 4-aminobenzoate compound of the mixture, said quantity n having a value in the range of from at least 1 to about 25;

wherein each said compound is bound to an insoluble, weakly acid, hydrogen form cation exchange resin in the form of a resinate;

wherein on a resin free basis, the weight of a bound butyl 4-aminobenzoate compound divided by the total weight of bound butyl 4-aminobenzoate compounds being defined as the bound weight fraction of said compound, and wherein said composition is capable of release of said bound butyl 4-aminobenzoate compounds from said resinate in simulated gastrointestinal dissolution, the weight of each said released compound divided by the total weight of released compounds being defined as the released weight fraction of said released compound, said released weight fractions when regressed against said bound weight fractions of the same compound said regression yields an index of determination, $R^2$, of at least about 0.90 and a confidence level less than about 0.1.

In a seventh embodiment, the invention is a composition of the invention comprising at least one additional pharmaceutically active agent bound to at least one ion exchange agent.

In an eighth embodiment, the invention is a composition of h invention additionally comprising a noxious tasting agent.

In a ninth embodiment, the invention is a solid oral dosage form pharmaceutical comprising a composition of the invention, wherein under the same conditions of simulated buccal dissolution, said dosage form shows a lower peak concentration of free butyl 4-aminobenzoate compounds than a quantity of unbound benzonatate equal to that in said dosage form.

The invention includes a method of making a composition of the invention, comprising the steps:

a) selecting a mixture of individual butyl 4-aminobenzoate compounds having the formula $C_4H_9$—NH—$C_6H_4$—COO—$(C_2H_4O)_n$—$CH_3$, and having the structure shown in FIG. 1; wherein the quantity n in the formula and in FIG. 1 is the number of ethoxy units in a butyl 4-aminobenzoate compound of the mixture, said quantity n having a value in the range of from at least 1 to about 25;

b) selecting an insoluble, weakly acid, hydrogen form cation exchange resin c) adding said selected mixture of butyl 4-aminobenzoate compounds and the selected weakly acid, hydrogen form cation exchange resin to a sufficient quantity of water to form a slurry wherein the weight ratio of butyl 4-aminobenzoate compounds to cation exchange resin is from about 0.2 to about 1.2 and the weight fraction of water in the slurry is from about 0.5 to about 0.8;

d) reacting said butyl 4-aminobenzoate compounds with said cation exchange resin at a temperature from about 18° C. to about 70° C. for sufficient time to bond said butyl 4-aminobenzoate compounds to said cation exchange resin to form a resinate with a loading efficiency of at least about 70 percent;

e) filtering said resinate from said slurry;

f) rinsing said resinate; and g) drying said resinate.

The invention also includes a method of for reducing or preventing adverse effects caused by a release of benzonatate into the oral cavity comprising treating a patient requiring an anti-tussive with a pharmaceutical composition of the invention.

BRIEF DESCRIPTION OF THE DRAWINGS

FIG. 3 is a Certificate of Analysis for a benzonatate supplied by Formosa Laboratories, Inc.

DETAILED DESCRIPTION OF THE INVENTION

The inventive compositions and oral dosage forms of benzonatate use ion exchange resin technology to diminish or eliminate the choking hazard and adverse events that would occur if the product were released in the oral mucosa. Further, the compositions and oral dosage forms of the invention release the constituent homologs of resinate-bound benzonatate into a human body in essentially the same proportions as existed in the original mixture of benzonatate homologs before resination.

However, not all ion exchange resins are satisfactory for this purpose. Ion-exchange resins may be cationic or anionic. Only cationic ion exchange resins are suitable for the purposes of the invention. Moreover, cationic ion exchange resins may be in the salt form or in the acid form. Surprisingly, only cationic ion exchange resins in the acid form have been found to meet the needs of the invention. Further, cationic ion exchange resins in the acid form may be "weak acids" having carboxyl functionality or they may be "strong acids" having sulfonic acid functionality. Yet more surprisingly, only ion exchange resins having "weak acid" carboxyl functionality have been found to provide all of the needs of the invention.

Figure 1:
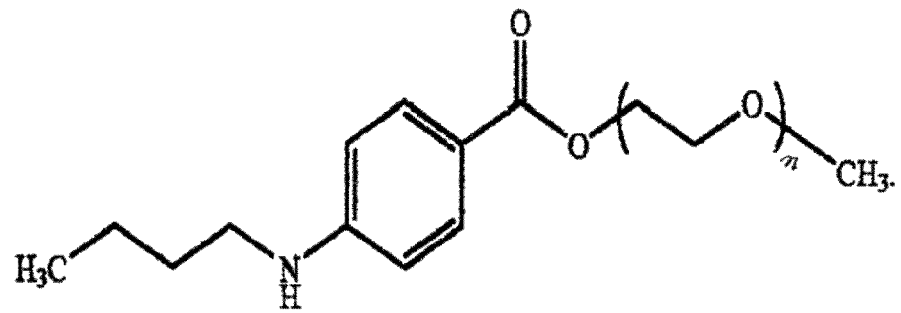
FIG. 1 illustrates the molecular structure of the butyl 5-aminobenzoate compounds comprising a benzonatate employed in the invention.

In a first embodiment, the invention is a resinate composition of matter comprising a mixture of individual butyl 4-aminobenzoate compounds having the formula $C_4H_9$—NH—$C_6H_4$—COO—$(C_2H_4O)_n$—$CH_3$ and the structure shown in FIG. 1;

wherein the quantity n in the formula and in FIG. 1 is the number of ethoxy units in a butyl 4-aminobenzoate compound of the mixture, said quantity n having a value in the range of from at least 1 to about 25; and wherein each said compound is bound to an insoluble, weakly acid, hydrogen form cation exchange resin in the form of a resinate.

In a second embodiment, the invention is a resinate composition of matter comprising a mixture of individual butyl 4-aminobenzoate compounds having the formula $C_4H_9$—NH—$C_6H_4$—COO—$(C_2H_4O)_n$—$CH_3$ and the structure shown in FIG. 1; wherein the quantity n in the formula and in FIG. 1 is the number of ethoxy units in a butyl 4-aminobenzoate compound of the mixture, said quantity n having a value in the range of from at least 1 to about 25;

wherein each said compound is bound to an insoluble, weakly acid, hydrogen form cation exchange resin in the form of a resinate; and wherein on a resin free basis, the weight of a bound butyl 4-aminobenzoate compound divided by the total weight of bound butyl 4-aminobenzoate compounds being defined as the bound weight fraction of said compound, a regression of the number of ethoxy units in said compounds against a normal distribution of said bound weight fractions yields an index of determination, $R^2$, of at least about 0.90, a confidence level less than about 0.1, said weight fractions having a peak in the range of from about 6 to about 12 ethoxy units.

Preferably, the index of determination, $R^2$, is at least about 0.94, and most preferably, at least about 0.98. Preferably, the regression has a significance level less than about 0.01, and most preferably, less than about 0001.

For the purposes of the invention, the distribution of homologs in a mixture of butyl 4-aminobenzoate homologs having different numbers of ethoxy groups is measured by high pressure liquid chromatography coupled with in-line ultra-violet spectroscopy using an AGILENT™ 1100 HPLC-UV system. The HPLC-UV measurements reported here were determined at Dow Chemical Company.

In a third embodiment, the invention is a resinate composition of matter comprising a mixture of individual butyl 4-aminobenzoate compounds having the formula $C_4H_9$—NH—$C_6H_4$—COO—$(C_2H_4O)_n$—$CH_3$ and the structure shown in FIG. 1;

wherein the quantity n in the formula and in FIG. 1 is the number of ethoxy units in a butyl 4-aminobenzoate compound of the mixture, said quantity n having a value in the range of from at least 1 to about 25;

wherein each said compound is bound to an insoluble, weakly acid, hydrogen form cation exchange resin in the form of a resinate; and wherein on a resin free basis, the weight of a bound butyl 4-aminobenzoate compound divided by the total weight of bound butyl 4-aminobenzoate compounds being defined as the bound weight fraction of said compound, said bound weight fractions when regressed against the weight fractions of the same compounds in the U.S. Food and Drug administration approved prescription drug benzonatate, said benzonatate listed in the F.D.A. Orange Book as Application No. N011210, said regression yields an index of determination, $R^2$, of at least about 0.90 and confidence level less than about 0.1

Preferably, the index of determination of this regression, $R^2$, is at least about 0.94, and most preferably, at least about 0.98. Preferably, the significance level of this regression is less than about 0.01, and most preferably, less than about 0.001. Preferably, this regression yields an F ratio at least about 50, preferably at least about 100, and most preferably, at least about 200.

In a fourth embodiment, the invention is a resinate composition of matter comprising a mixture of individual butyl 4-aminobenzoate compounds having the formula $C_4H_9$—NH—$C_6H_4$—COO—$(C_2H_4O)_n$—$CH_3$ and the structure shown in FIG. 1;

wherein the quantity n in the formula and in FIG. 1 is the number of ethoxy units in a butyl 4-aminobenzoate compound of the mixture, said quantity n having a value in the range of from at least 1 to about 25;

wherein each said compound is bound to an insoluble, weakly acid, hydrogen form cation exchange resin in the form of a resinate; and wherein said composition is capable of release of said bound butyl 4-aminobenzoate compounds from said resinate in simulated gastrointestinal dissolution, the weight of each said released compound divided by the total weight of released compounds being defined as the released weight fraction of said compounds, said released weight fractions when regressed against the weight fractions of the same compound in the U.S. Food and Drug administration approved prescription drug benzonatate, said benzonatate listed in the F.D.A. Orange Book as Application No. N011210, said regression yields an index of determination, $R^2$, of at least about 0.90, and a significance level less than about 0.1.

Preferably, the index of determination of this regression, $R^2$, is at least about 0.94, and most preferably, at least about 0.98. Preferably, the significance level of this regression is less than about 0.01, and most preferably, less than about 0.001. Preferably, this regression yields an F ratio at least about 50, preferably at least about 100, and most preferably, at least about 200.

In a fifth embodiment, the invention is a resinate composition of matter comprising a mixture of individual butyl 4-aminobenzoate compounds having the formula $C_4H_9$—NH—$C_6H_4$—COO—$(C_2H_4O)_n$—$CH_3$ and the structure shown in FIG. 1;

wherein the quantity n in the formula and in FIG. 1 is the number of ethoxy units in a butyl 4-aminobenzoate compound of the mixture, said quantity n having a value in the range of from at least 1 to about 25;

wherein each said compound is bound to an insoluble, weakly acid, hydrogen form cation exchange resin in the form of a resinate; and wherein on a resin free basis, the weight of a bound butyl 4-aminobenzoate compound divided by the total weight of bound butyl 4-aminobenzoate compounds being defined as the bound weight fraction of said compound, said bound weight fractions when regressed against the weight fractions of the same compounds in the mixture of free butyl 4-aminobenzoate compounds from which the resinate composition was made, said regression yields an index of determination, $R^2$, of at least about 0.90 and confidence level less than about 0.1.

Preferably, the index of determination of this egression, $R^2$, is at least about 0.94, and most preferably, at least about 0.98. Preferably, the significance level of this regression is less than about 0.01, and most preferably, less than about 0.001. Preferably, this regression yields an F ratio at least about 50, preferably at least about 100, and most preferably, at least about 200.

In a sixth embodiment, the invention is a resinate composition of matter comprising a mixture of individual butyl 4-aminobenzoate compounds having the formula. $C_4H_9$—NH—$C_6H_4$—COO—$(C_2H_4O)_n$—$CH_3$ and the structure shown in FIG. 1;

wherein the quantity n in the formula and in FIG. 1 is the number of ethoxy units in a butyl 4-aminobenzoate compound of the mixture, said quantity n having a value in the range of from at least 1 to about 25;

wherein each said compound is bound to an insoluble, weakly acid, hydrogen form cation exchange resin in the form of a resinate;

wherein on a resin free basis, the weight of a bound butyl 4-aminobenzoate compound divided by the total weight of bound butyl 4-aminobenzoate compounds being defined as the bound weight fraction of said compound, and wherein said composition is capable of release of said bound butyl 4-aminobenzoate compounds from said resinate in simulated gastrointestinal dissolution, the weight of each said released compound divided by the total weight of released compounds being defined as the released weight fraction of said released compound, said released weight fractions when regressed against said bound weight fractions of the same compound said regression yields an index of determination, $R^2$, of at least about 0.90 and a confidence level less than about 0.1.

Preferably, the index of determination of this regression, $R^2$, is at least about 0.94, and most preferably, at least about 0.98. Preferably, the significance level of this regression is less than about 0.01, and most preferably, less than about 0.001. Preferably, this regression yields an F ratio at least about 50, preferably at least about 100, and most preferably, at least about 200.

In a seventh embodiment, the invention is a composition of the invention comprising at least one additional pharmaceutically active agent bound to at least one ion exchange agent.

In an eighth embodiment, the invention is a composition of the invention additionally comprising a noxious tasting agent.

In a ninth embodiment, the invention is a solid oral dosage form pharmaceutical comprising a composition of the invention, wherein under the same conditions of simulated buccal dissolution, said dosage form shows a lower peak concentration of free butyl 4-aminobenzoate compounds than a quantity of unbound benzonatate equal to that in said dosage form.

Figure 2:
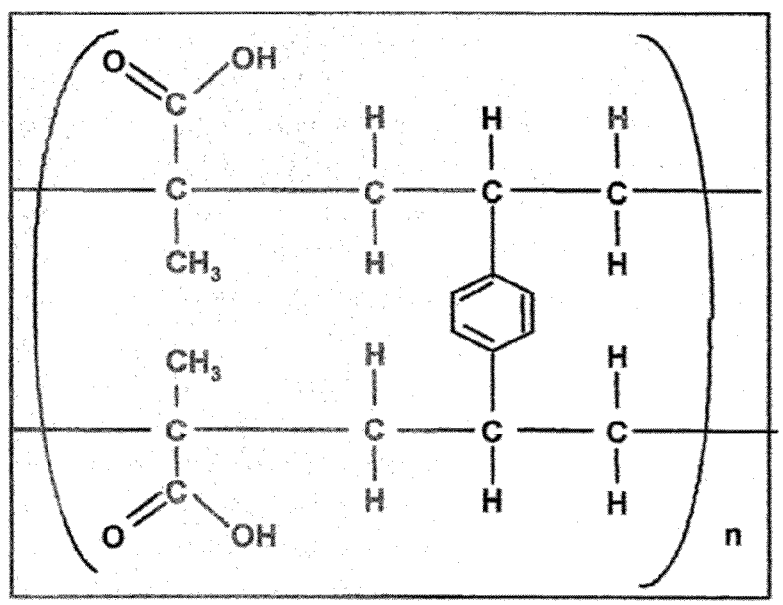
FIG. 2 is the structure of a weakly acid hydrogen form ion exchange resin employed in the invention.

In each of the above embodiments, the insoluble, weakly acid, hydrogen form cation exchange resin is preferably a polyacrylic resin having the structural formula shown in FIG. 2.

The invention includes a method of making a composition of the invention, comprising the steps:
  a) selecting a mixture of individual butyl 4-aminobenzoate compounds having the formula $C_4H_9$—NH—$C_6H_4$—COO—$(C_2H_4O)$—$CH_3$, and having the structure shown in FIG. 1; wherein the quantity n in the formula and in FIG. 1 is the number of ethoxy units in a butyl 4-aminobenzoate compound of the mixture, said quantity n having a value in the range of from at least 1 to about 25;
  b) selecting an insoluble, weakly acid, hydrogen form cation exchange resin
  c) adding said selected mixture of butyl 4-aminobenzoate compounds and the selected weakly acid, hydrogen form cation exchange resin to a sufficient quantity of water to form a slurry wherein the weight ratio of butyl 4-aminobenzoate compounds to cation exchange resin is from about 0.2 to about 1.2 and the weight fraction of water in the slurry is from about 0.5 to about 0.8;
  d) reacting said butyl 4-aminobenzoate compounds with said cation exchange resin at a temperature from about 18° C. to about 70° C. for sufficient time to bond said butyl 4-aminobenzoate compounds to said cation exchange resin to form a resinate with a loading efficiency of at least about 70 percent;
  e) filtering said resinate from said slurry;
  f) rinsing said resinate; and
  g) drying said resinate.

Preferably, in step a) of the inventive method, the selected mixture of butyl 4-aminobenzoate compounds meets the identification and physical test specifications of benzonatate as specified in USP 28.

More preferably, for the selected mixture in step a), the weight fractions of butyl 4-aminobenzoate compounds when regressed against the weight fractions of the same compound in the U.S. Food and Drug administration approved prescription drug benzonatate, said benzonatate listed in the F.D.A. Orange Book as Application No. N011210, said regression yields an index of determination, $R^2$, of at least about 0.90, preferably at least about 0.94 and most preferably, at least about 0.98, and a confidence level less than about 0.1, preferably less than about 0.01 and most preferably, less than about 0.001.

The invention also includes a method of for reducing or preventing adverse effects caused by a release of benzonatate into the oral cavity comprising treating a patient requiring an anti-tussive with a pharmaceutical composition of the invention.

The inventive dosage forms can be either immediate release or extended release formulations or both in one medicament.

In each embodiment of the invention, the quantity n representing the number of ethoxy groups on a butyl 4-amino compound is preferably from 2 to about 25. More preferably, n is from 2 to about 20, Most preferably, n is from about 3 to about 17.

Strong acid resins are so named because their chemical behavior is similar to strong acids. During the process of creating the resin polymer, a strong acid such as $SO_3H$ is introduced into the resin. This sulfonic acid group is very highly ionizable and thus produces many ions available for the exchange process during drug resination.

In a weak acid resin the ionizable group introduced to the polymer is a carboxylic acid (COOH) as opposed to the sulfonic acid group ($SO_3H$) used in strong acid resins. These resins behave similarly to weak organic acids so are weakly dissociated i.e. have fewer ions available for exchange.

An acid dissociation constant, $pK_a$, (also known as acidity constant, or acid-ionization constant) is a quantitative measure of the strength of an acid in solution. The larger the value of $pK_a$, the smaller the extent of dissociation. A strong acid such as $SO_3H$ pKa is approximately 0. A weak acid such COOH has pKa in the range of 4.0 to 7.0.

The immediate and extended release oral dosage products described here are a multi-particulate system composed of benzonatate bound to ion exchange resin particles that improves the safety profile of benzonatate as currently marketed and therefore increase its usefulness in the treatment of cough.

Ion exchange is a reversible chemical reaction wherein an ion (an atom or molecule that has lost or gained an electron and thus acquired an electrical charge) from solution is exchanged for a similarly charged ion attached to an immobile solid particle.

A synthetically produced organic ion-exchange resin is an insoluble matrix (or support structure) normally in the form of small (1-2 mm diameter) beads, and fine (1-300 μm) powders usually white or yellowish, fabricated from an organic polymer substrate. The trapping of ions takes place only with simultaneous releasing of other ions; thus the process is called ion-exchange. This ion exchange process can take place throughout the polymeric matrix and is not restricted only to the surface. This gives synthetically produced organic ion exchange resins high ion exchange capacity. Ion exchange resins can have gellular (no separate pore phase) or porous polymer matrices.

Ion exchange particles can also be naturally occurring inorganic zeolites. The synthetic organic resins are the predominant type used today because their characteristics can be tailored to specific applications.

Ion exchange resins are classified as cation exchangers, that have positively charged mobile ions available for exchange, and anion exchangers, whose exchangeable ions are negatively charged. Both anion and cation resins are produced from the same basic organic polymers. They differ in the ionizable group attached to the hydrocarbon network. It is this functional group that determines the chemical behavior of the resin. Resins can be broadly classified as strong or weak acid cation exchangers or strong or weak base anion exchangers.

A benzonatate resinate is achieved by an ionic binding of the benzonatate molecules to the resin bead. The benzonatate molecules will only disassociate from the resin in the presence of an acidic environment and/or a strong electrolyte solution e.g. NaCl, both of which are found in the stomach. In the oral cavity, saliva is normally alkaline, with a pH of 7.2 or above. In addition the oral cavity has a low concentration of strong ionic species such as NaCl. As noted, an acidic environment and/or a strong electrolyte solution are necessary for the benzonatate molecules to disassociate from the resinate beads. Because the ion exchange process is stoichiometric, the small number of available ions means that few benzonatate ions can be released into the oral cavity. Therefore, one would not expect significant disassociation of the resin complex in the oral cavity as compared to the gastric environment. Additionally, simple mechanical forces, such as created by chewing or sucking, will not cause the benzonatate molecules to disassociate from the resinate beads. Only a chemical process in an acidic environment and/or the presence of strong ionic species can cause such a disassociation. Therefore, a formulation of benzonatate with a weak or strong acid resin significantly diminishes or entirely eliminates the hazards associated with benzonatate being released into the oral mucosa. The addition of denatonium benzoate or similar noxious tasting agent further decreases the tendency for a patient to chew or suck a benzonatate tablet or capsule.

A noxious tasting agent such as denatonium benzoate has an extremely bitter taste and should the patient chew the product, a very unpleasant taste is created in the oral cavity. This may cause the patient to cease chewing or sucking the medicament and may cause a reflexive expectoration of the medicament. The noxious tasting agent can be, for example, denatonium benzoate, cayenne pepper or capsaicin.

An oral dosage composition of the invention can be formulated, for example, as a capsule or compressed tablet. The inventive compositions are preferably in a solid oral dosage form, such as a tablet, caplet or capsule containing benzonatate bound to an ion exchange resin and, optionally, a noxious tasting agent added to further deter chewing or sucking on the solid oral dosage form.

Weak acid ion exchange resins useful in the invention include, for example, Amberlite IRP64, DOWEX MAC-3, but other weak acid ion exchange agents in the acid ($H^+$) form may be used.

Strong acid ion exchange resins and weak acid ion exchange resins in the salt form are believed to be much less useful in accomplishing all of the objectives of the invention. As will be seen, butyl 4-aminobenzoate resinates prepared from strong acid resins in the acid form release too little of the drug in simulated gastrointestinal dissolution to be useful. The salt form of both strong and weak acid ion exchange resins showed essentially no capacity for resination by benzonatate.

The invention further includes compositions including both an immediate release (IR) component and extended release (ER) component. The oral dosage composition can optionally include a second ion exchange resin. This second ion exchange resin is bound to one or more pharmaceutical agents other than benzonatate and can be coated with an extended release coating, resulting in extended release of the pharmaceutically active agent(s) from the second ion exchange resin when administered to a patient. The second ion exchange resin may be a cationic or anionic resin chosen to be suitable to the pharmaceutical agent(s) involved.

By "F.D.A. Orange Book" is meant the "Orange Book: Approved Drug Products with Therapeutic Equivalence Evaluations" $32^{nd}$ Edition, 2012, published by the Food and Drug Administration.

TESSALON™ is the proprietary name of the benzonatate capsule listed in the F.D.A. Orange book as Application No. N011210.

By "pharmaceutically active agent" is meant agents other than food articles that are intended to diagnose, cure, mitigate, treat or prevent disease in man or other animals or that are intended to affect the structure or any function of the body of man or other animals that are physiologically acceptable. The agent could be a combination of drug therapies as well as a single agent.

By "noxious tasting agent" is meant an agent that, when released into the oral cavity is bitter, foul tasting, pepper like or any other agent that is otherwise safe and physiologically acceptable but has a very bad taste.

By "physiologically acceptable" is meant those substances that are adequately tolerated without causing unacceptable negative side effects.

By "resinate" is meant the complex formed when a drug reacts with a resin particle in the stoichiometric process described above and a drug/resin complex is formed.

By "immediate release" is meant that the pharmacologically active agent is released from the formulation immediately such that 80%, 85%, 90%, or even 95% of the pharmaceutically active agent in the formulation is released within 45 minutes when dissolution is measured according to the USP 31 NF 26 section 711.

By "extended release" is meant that the pharmaceutically active agent is released from the formulation at a controlled rate such that the formulation allows for a reduction in dosing frequency as compared to that presented by a conventional dosage form, e.g. an immediate release dosage form.

Noxious Tasting Agents

The drug-containing ion exchange resins of the invention may be also formulated with noxious tasting agents. These noxious tasting agents are designed to deter chewing or sucking of the solid oral dosage form Examples of suitable noxious tasting agents are:
  Denatonium benzoate
  Cayenne pepper
  Capsaicin Pharmaceutically Active Agents The invention features methods and compositions for immediate and extended release of pharmaceutically active agents using an ion exchange resin with benzonatate and one or more of the following pharmaceutically active agents:

A: Anti-tussives, e.g., caramiphen edisylate, chlophedianol, codeine, dextromethorphan hydrobromide, hydrocodone, levopropoxyphene, morphine, codeine, ethylmorphine, dihydrocodeine, benzylmorphine, laudanum, dihydroisocodeine, nicocodeine, nicodicodeine, hydrocodone, hydromorphone, acetyldihydrocodeine, thebacon, diamorphine (heroin), acetylmorphone, noscapine, and pholcodine.

B: Narcotic analgesics, e.g., codeine, oxycodone, hydrocodone, diamorphine, pethidine, morphine, oxymorphone, nalorphine, naloxone, naltrexone, opium, hydromorphone, nicomorphine, dihydrocodeine, and papaveretum.

C: Decongestants, e.g., pseudoephedrine hydrochloride, phenylephrine bitartrate, and pseudoephedrine sulfate.

D: Non-steroidal anti-inflammatory drugs, e.g., aspirin, magnesium salicylate, diclofenac, etodolac, indometacin, nabumetone, sulindac, tolmetin, ibuprofen, ketoprofen, mefenamic acid, meclofenamic acid, phenylbutazone, piroxicam, meloxicam, celecoxib, parecoxib, rofecoxib, valdecoxib, and naproxen sodium.

E: Anti-emetic drugs, e.g., dolasetron, granisetron, ondansetron, tropisetron, palonosetron, mirtazapine, metoclopramide, cyclizine, diphenhydramine, dimenhydrinate, meclizine, promethazine, and hydroxyzine.

F: Anti-histamines, e.g., diphenhydramine, loratadine, desloratadine, meclizine, fexofenadine, pheniramine, cetirizine, promethazine, and chlorpheniramine.

G: Proton pump inhibitors (PPI), e.g., omeprazole, esomeprazole, pantoprazole, lansoprazole, and rabeprazole.

H: H2 Antagonists, e.g., cimetidine, ranitidine, and famotidine.

I: Anti-depressants, e.g., citalopram, escitalopram, fluoxetine, fluvoxamine, paroxetine, sertraline, desvenlafaxine, duloxetine, milnacipran, venlafaxine, atomoxetine, mazindol, reboxetine, viloxazine, amitriptyline, clomipramine, doxepin, imipramine, trimipramine, desipramine, nortriptyline, protriptyline, moclobemide, phenelzine, and selegiline.

J: Tranquilizers, e.g., amobarbital, pentobarbital, secobarbital, phenobarbital, clonazepam, diazepam, estazolam, flunitrazepam, lorazepam, midazolam, nitrazepam, oxazepam, triazolam, temazepam, chlordiazepoxide, and alprazolam.

K: Anti-convulsants, e.g., felbamate, carbamazepine, oxcarbazepine, vigabatrin, progabide, tiagabine, topiramate, gabapentin, pregabalin, ethotoin, and phenyloin.

L: Hypnotics, e.g., zolpidem, zaleplon, zopiclone, and eszopiclone.

M: Muscle relaxants, e.g., methocarbamol, carisoprodol, chlorzoxazone, cyclobenzaprine, gabapentin, metaxalone, and orphenadrine.

N: Anti-psychotics, e.g., haloperidol, droperidol, chlorpromazine, fluphenazine, perphenazine, prochlorperazine, thioridazine, trifluoperazine, mesoridazine, promazine, triflupromazine, levomepromazine, methotrimeprazine, pimozide, chlorprothixene, flupenthixol, thiothixene, zuclopenthixol, clozapine, olanzapine, risperidone, quetiapine, ziprasidone, amisulpride, asenapine, and paliperidone.

O: Anti-microbials, e.g., EDTA, zinc compounds, triclosan, domiphen, cetyl pyridium chloride, domiphen bromide, fluorides, alexidine, and octenidine.

P: Anti-diarrheals, e.g., bismuth subsalicylate and loperamide.

R: CNS stimulants, e.g., caffeine, cocaine, and amphetamines.

S: Attention Deficit and Hyperactivity Disorder drugs, e.g., methylphenidate, dextroamphetamine sulfate, amphetamine, and atomoxetine hydrochloride.

The invention also includes methods and compositions for delivering combinations of pharmaceutically active compounds. Examples of such combinations are:

A: benzonatate and an antihistamine
B: benzonatate and a decongestant
C: benzonatate and an analgesic
D: benzonatate and an NSAID
E: benzonatate and an antihistamine and a decongestant
F: benzonatate and an antihistamine and an analgesic
G: benzonatate and an antihistamine and an NSAID
H: benzonatate and an antihistamine and a decongestant and an analgesic Dosage Forms Suitable dosage forms include tablets, capsules, orally disintegrating tablets, powders, beadlets, and the like.

EXAMPLES

It will be understood in the following examples that the quantity indicated by the nomenclature aE-b is equivalent to the quantity $(a \cdot 10^{-b})$, i.e., the quantity a times the quantity 10 to the minus b power.

Example 1

A benzonatate was purchased from Formosa Laboratories Inc., Taiyuan, Taiwan meeting the identification and test specifications of USP 28. The Certificate of Analysis (COA) shown in FIG. 3 gives the percentage of butyl 4-aminobenzoate homologs in the benzonatate in mol percent. Calculation of the weight fraction of each of the homologs from the mol percents given in the COA is shown in Table I below.

The distribution of homologs in a mixture of butyl 4-aminobenzoate homologs having different numbers of ethoxy groups was determined at Dow Chemical Company by high pressure liquid chromatography coupled with in-line ultraviolet spectroscopy using an AGILENT™ 1100 HPLC-UV system. The HPLC-UV conditions of determination were as follows:

Column: PHENOMENEX™ C18, 4.6×150 mm
UV Wavelength: 310 nm
Mobile Phase: 0.04M $KH_2PO_4$:acetonitrile; (1:1)
(HPLC grade acetonitrile, Fisher Part No. P285)
Flow Rate: 0.5 ml/min
Temperature: Normal laboratory conditions (ambient)
Diluent: $H_2O$
Injection Volume: 20 μL The HPLC/UV output is a plot of UV intensity versus time showing peaks corresponding to elution of individual homologs, and also a table of the area of those peaks. The area percent for the peak corresponding each homolog is proportional to its mol percent in the mixture. This is converted to a weight fraction as follows:

The last column of Table I below shows the weight fractions of butyl 4-aminobenzoate homologs in the Formosa benzonatate determined by the HPLC-UV method.

TABLE I

Weight Distribution of Homologs in Formosa Benzonatate

| No. Ethoxy Units | Mol Wt. | COA Mol. % | Basis: 1 mol Wt. | COA Wt. Fr. | HPLC-UV Wt. Fr. |
|---|---|---|---|---|---|
| 1 | 251 | | | | |
| 2 | 295 | | | | |
| 3 | 339 | 0 | 0 | 0.0000 | 0.0022 |
| 4 | 383 | 2 | 7.66 | 0.0122 | 0.0106 |
| 5 | 427 | 4 | 17.08 | 0.0272 | 0.0293 |
| 6 | 471 | 8 | 37.68 | 0.0600 | 0.0612 |
| 7 | 515 | 12 | 61.8 | 0.0984 | 0.1031 |
| 8 | 559 | 15 | 83.85 | 0.1336 | 0.1380 |
| 9 | 603 | 16 | 96.48 | 0.1537 | 0.1545 |
| 10 | 647 | 14 | 90.58 | 0.1443 | 0.1486 |
| 11 | 691 | 11 | 76.01 | 0.1211 | 0.1273 |
| 12 | 735 | 8 | 58.8 | 0.0937 | 0.0925 |
| 13 | 779 | 6 | 46.74 | 0.0744 | 0.0614 |
| 14 | 823 | 3 | 24.69 | 0.0393 | 0.0368 |
| 15 | 867 | 2 | 17.34 | 0.0276 | 0.0198 |
| 16 | 911 | 1 | 9.11 | 0.0145 | 0.0101 |
| 17 | 955 | 0 | 0 | 0.0000 | 0.0045 |
| Sum wts. = | | | 627.82 | 1.0000 | 0.9999 |

Regression of the weight fractions of homologs measured by the HPLC-UV method against the weight fractions calculated from the COA yielded an index of determination, $R^2$, of 0.986, an F ratio of 937 and a significance of 1.7E-13 ($1.7 \times 10^{-13}$) validating the HPLC-UV method of analysis used here.

Example 2

A resination reaction of the Formosa benzonatate was carried out as follows:

0.3306 g of a weak acid ion-exchange resin in the acid form having the structure shown in FIG. 2 (IRP64H from Dow Chemical) was dispersed in 1.23 g of distilled water to form a uniform slurry. 0.1665 g of the Formosa benzonatate was added with stirring. The mixture was stirred at room temperature for 40 hours to react the benzonatate and resin thereby forming a resinate. The slurry was vacuum filtered and both the resinate and the filtrate were collected. The resinate particles were washed by displacement of approximately two equal volumes of deionized water and the wash water was added to the filtrate. The resinate was dried to constant weight at 55° C.

The weight of each homolog bound in this resinate of the invention was determined as follows:

Wt. of bound homolog=Initial wt. of homolog−wt. of un-reacted homolog

The initial weight of a homolog was the weight of benzonatate (0.1665 g in this example) times the weight fraction of the homolog from the last column of Table I.

The weights of the individual un-reacted butyl 4-aminobenzoate homologs were measured by HPLC-UV analysis of the filtrate.

The weight fraction of a bound homolog in the resinate, defined as the weight, on a resin free basis, of a bound homolog divided by the total weight, of bound homologs, also on a resin free basis is shown in Table II below in comparison with the weight fractions of homologs in the initial benzonatate.

TABLE II

Distribution of Homologs in Benzonatate and in Resinate

| No. Ethoxy Units | Wt. Fr. in Formosa Benzonatate | Wt. Fr. in Resinate of Invention |
|---|---|---|
| 3 | 0.0022 | 0.002 |
| 4 | 0.0106 | 0.011 |
| 5 | 0.0293 | 0.029 |
| 6 | 0.0612 | 0.061 |
| 7 | 0.1031 | 0.103 |
| 8 | 0.1380 | 0.138 |
| 9 | 0.1545 | 0.155 |
| 10 | 0.1486 | 0.149 |
| 11 | 0.1273 | 0.127 |
| 12 | 0.0925 | 0.093 |
| 13 | 0.0614 | 0.061 |
| 14 | 0.0368 | 0.037 |
| 15 | 0.0198 | 0.019 |
| 16 | 0.0101 | 0.010 |
| 17 | 0.0045 | 0.005 |
| Sum | 0.9999 | 0.999 |

Regression of the weight fraction of homologs bound in the resinate against the weight fraction of the homologs in the initial benzonatate yielded an index of determination, $R^2$, of 0.9999 an F ratio of 281,000 and a significance of 1.4E-29 ($1.4 \times 10^{-29}$) It will be seen that the distribution of homologs in the resinate matched the distribution of homologs in the initial benzonatate almost exactly. It is believed that this is a novel result without counterpart in the prior art.

Drug loading on the resin was the sum of weights of bound homologs divided by the weight of resin. Drug loading was 0.386 mg/mg.

Loading efficiency was determined by the total weight of loaded drug divided by the initial weight of drug times one hundred. Loading efficiency was 98.7%

The number of ethoxy units in the bound homologs in the resinate was regressed against a normal distribution of their weight fractions yielding an index of determination, $R^2$, of 0.997, an F ratio of 4,393 and a significance of 9.2E-17. Thus, the weight distribution of bound homologs was a normal distribution function of the number of ethoxy units in the homolog to a high degree of precision.

The weight distribution of bound homologs in the resinate of the invention was also compared with the distribution found in the F.D.A. approved prescription drug listed in the F.D.A. Orange Book as Application No. 11210 and having a trade name of. TESSALON™. The benzonatate was removed from a TESSALON™ capsule by syringe and analyzed by HPLC-UV. The analysis of this F.D.A. approved benzonatate is shown in Table III alongside of the distribution of bound homologs in the resinate of the invention.

TABLE III

Distribution of Homologs in TESSALON ™ and in Resinate

| No. Ethoxy Units | Wt. Fr. in TESSALON ™ Benzonatate | Wt. Fr. in Resinate of Invention |
|---|---|---|
| 3 | 0.0004 | 0.002 |
| 4 | 0.0049 | 0.011 |
| 5 | 0.0251 | 0.029 |
| 6 | 0.0685 | 0.061 |
| 7 | 0.118 | 0.103 |
| 8 | 0.1579 | 0.138 |
| 9 | 0.1705 | 0.155 |
| 10 | 0.1573 | 0.149 |
| 11 | 0.126 | 0.127 |
| 12 | 0.0868 | 0.093 |
| 13 | 0.0496 | 0.061 |
| 14 | 0.0228 | 0.037 |
| 15 | 0.0084 | 0.019 |
| 16 | 0.0026 | 0.01 |
| 17 | 0.0011 | 0.005 |
| Sum | 0.9999 | 0.999 |

Figure 4:
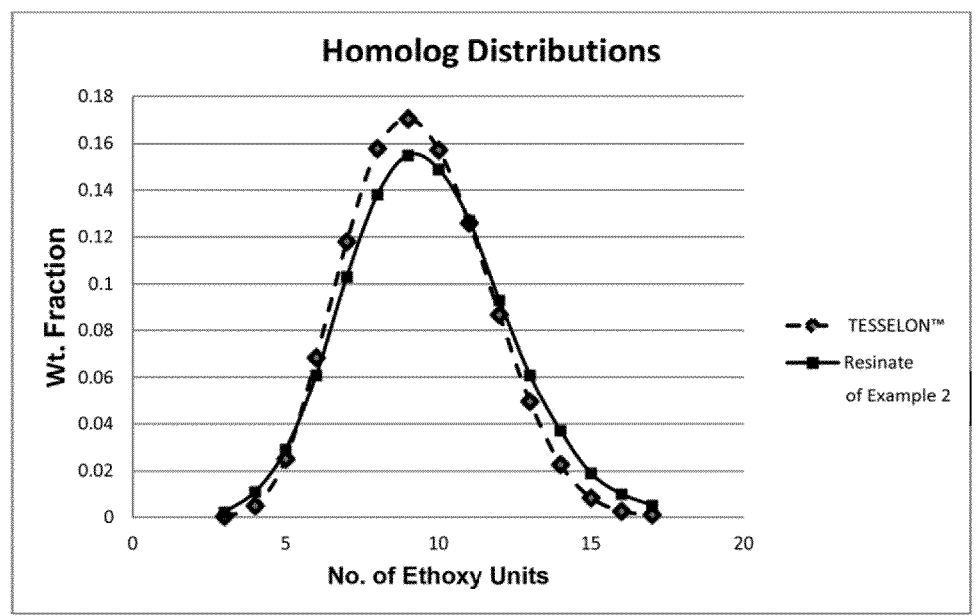
FIG. 4 shows the homolog distributions in the prescription drug "TESSALON" and bound in the resinate of Example 2 of the invention.

Regression of the weight fraction of homologs bound in the resinate against the weight fraction of the homologs in the TESSALON™ benzonatate yielded an index of determination, $R^2$, of 0.986, an F ratio of 947 and a significance of 1.6E-13. A plot of these distributions is shown in FIG. 4. It will be seen that the two distributions are in excellent agreement. A benzonatate resinate having a distribution of bound homologs in excellent agreement with the distribution in a benzonatate listed in the F.D.A. Orange book is believed to be a novel result without counterpart in the prior art.

Examples 3-8 and Comparative Examples 1-7

A series of resination reactions were carried out using the Formosa benzonatate. The reaction conditions varied in the resinations were as follows:
the ion-change resin;
 a) a strong acid resin consisting of cross-linked polystyrene sulfonate and designated IRP 69H
 b) a weak acid resin consisting of cross-linked polymethacrylic acid having the structural formula shown in FIG. 2, and designated IRP 64H
 both resins from Dow Chemical and both in the acid ($H^+$) form
the quantity of resin
the quantity of benzonatate (Wt. Benz)
the quantity of distilled water
the reaction time
All the resination reactions were carried out at room temperature.

The reaction procedure was as described in Example 2 except for the variation in the reaction conditions noted above.

The weights of the individual un-reacted butyl 4-aminobenzoate homologs were measured by HPLC-UV analysis of the filtrates and the weight of each homolog bound in the resinates was determined as described in Example 2. The weights of reactants, reaction times, and the loading and loading efficiencies are given in Table IV. below.

The last column of Table IV is a qualitative description of the match between the homolog distribution in the resinate and in the initial benzonatate. The term, "skewed lower" means that the distribution of homologs in the resinate was distributed more heavily toward lower numbers of ethoxy groups than in the initial benzonatate. Since the lower homologs are more basic than the higher homologs and should react with the acidic resin more readily, skewing of the bound distribution toward lower homologs would be expected. The term "match" means that regression of the weight fraction of homologs bound in the resinate against the weight fraction of the homologs in the initial benzonatate yielded an index of determination, $R^2$, of at least 0.90. Matching of the distribution of bound homologs with the distribution in the initial benzonatate is a surprising result.

The statistics of the regressions for each of the Examples and Comparative Examples are shown in Table IV. The distribution of homologs in the resinates and in the benzonatate from which they were made is shown in Table V.

Figure 5:
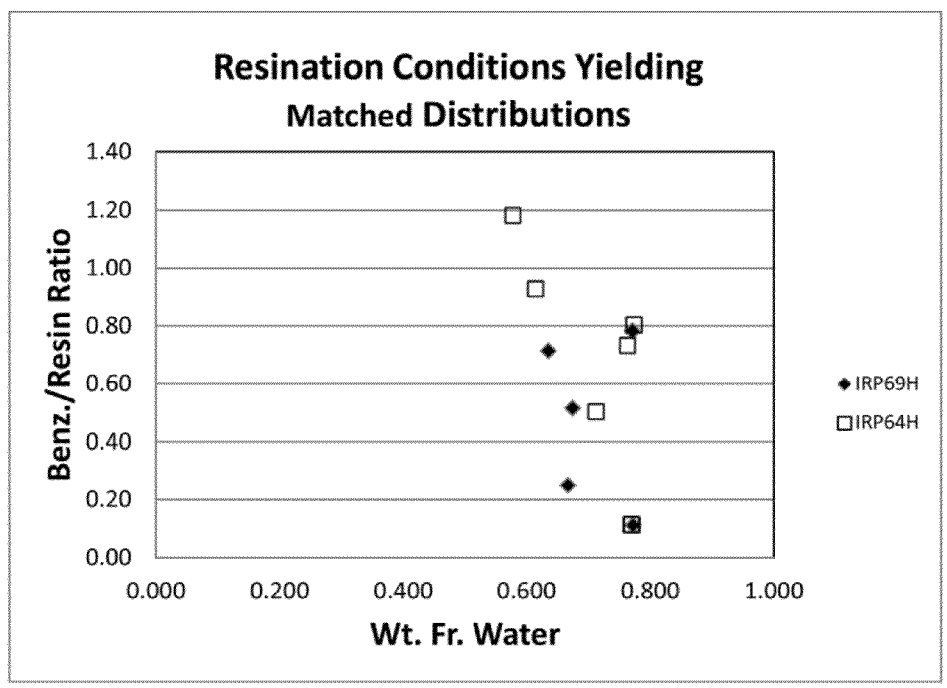
FIG. 5 shows the resination conditions for which the distribution of homologs in the resinate matches that in the benzonatate from which it is made.

The resination conditions that yielded a match between the homolog distributions in the resinate and the benzonatate from which it was made are shown in FIG. 5. It is seen that a match of homolog distributions was obtained when the benzonatate to resin ratio was from about 0.1 to about 1.2 and the weight fraction of water was from about 0.55 to about 0.85.

Example 9 and Comparative Example 8

Simulated Buccal Dissolution Testing

Most USP dissolution tests use large volumes of media—defined as 'sink conditions'; the aim is to get complete dissolution of the active ingredient. However, there are a number of factors that are unique to characterizing buccal dissolution that do not apply to GI dissolution. They are:
Small volume
Short residence time
Solids transfer
Composition
Incomplete dissolution For buccal dissolution the volume of saliva is very small compared to that of the stomach and the residence time in the mouth is also very short, the bulk of the dosage form being swallowed within a minute. The dissolution test used here employed procedures and a buccal dissolution apparatus devised by DOW Chemical described in U.S. Pat. No. 7,470, 545 B2 herein incorporated by reference to the extent not incompatible herewith.

In order for this test to give meaningful results it is necessary to use a dissolution media that simulates saliva. There is no USP recommended simulated saliva, so the composition

TABLE IV

| Example or Comparative Example | Resin | Wt. Bz, g | Wt. Resin, g | Water, g | Loading Time, hrs | Loading, mg/mg | Loading Efficiency | RSq, Resinate v. Benz | F Ratio | Significance | Ethoxy Dist. In Resinate |
|---|---|---|---|---|---|---|---|---|---|---|---|
| Comp 1 | 69H | 0.317 | 0.3468 | 0.7 | 40 | 0.344 | 54..0 | 0.61 | 20 | 0.006 | skewed lower |
| Comp. 2 | 69H | 0.4169 | 0.3473 | 0.7 | 40 | 0.226 | 22.5 | 0.53 | 15 | 0.0020 | skewed lower |
| Comp. 3 | 69H | 0.5 | 2 | 5 | 70 | 0.209 | 59.6 | 0.9997 | 42,000 | 3.E-24 | match |
| Comp. 4 | 69H | 0.98 | 1.9 | 5.96 | 70 | 0.34 | 58.7 | 0.9996 | 34,000 | 1.E-23 | match |
| Comp. 5 | 69H | 1.43 | 2 | 5.97 | 70 | 0.402 | 84.7 | 0.981 | 670 | 1.E-12 | slightly lower |
| Comp. 6 | 69H | 0.7985 | 1.0196 | 6.1206 | 17 | 0.405 | 73.9 | 0.9994 | 200,000 | 3.E-22 | match |
| Comp. 7 | 69H | 0.3669 | 3.2951 | 12.3857 | 17 | 0.111 | 96.5 | 0.9999 | 137,000 | 1.E-27 | match |
| Ex. 3 | 64H | 0.2716 | 0.2931 | 0.9 | 40 | 0.477 | 92.4 | 0.9996 | 37,000 | 7.E-24 | match |
| Ex. 4 | 64H | 0.3564 | 0.3015 | 0.9 | 40 | 0.5 | 79.6 | 0.999 | 13,000 | 7.E-21 | match |
| Ex. 5 | 64H | 0.8041 | 0.9998 | 0.1554 | 23 | 0.443 | 93.1 | 0.996 | 30,000 | 3.E-23 | match |
| Ex. 6 | 64H | 0.3727 | 3.3014 | 12.2985 | 23 | 0.107 | 99.69 | 0.9999 | 352,000 | 3.E-30 | match |
| Ex. 7 | 64H | 2.43 | 3.31 | 18.46 | 17 | 0.427 | 95.5 | 0.9999 | 106,000 | 8.E-27 | match |
| Ex. 8 | 64H | 2.25 | 20.01 | 73.95 | 14 | 0.087 | 79.4 | 0.997 | 5,100 | 3.E-18 | match |

TABLE V

Weight Percents of Homologs in Benzonatate and Resinates

| No. Ethoxy Units | Benz., | Comp. 1 | Comp. 2 | Comp. 3 | Comp. 4 | Comp. 5 | Comp. 6 | Comp. 7 | Ex. 3 | Ex. 4 | Ex. 5 | Ex. 6 | Ex. 7 | Ex. 8 |
|---|---|---|---|---|---|---|---|---|---|---|---|---|---|---|
| 3 | 0.22 | 0.43 | 0.41 | 0.2 | 0.2 | 0.3 | 0.2 | 0.2 | 0.2 | 0.1 | 0.2 | 0.2 | 0.2 | 0.3 |
| 4 | 1.06 | 4.22 | 2.31 | 1.1 | 1.1 | 1.2 | 1 | 1.1 | 1 | 0.9 | 1.1 | 1.1 | 1.1 | 1.2 |
| 5 | 2.93 | 5.19 | 6.32 | 2.9 | 3 | 3.4 | 2.8 | 3 | 2.9 | 2.8 | 3 | 2.9 | 3 | 3.2 |
| 6 | 6.12 | 10.61 | 12.36 | 6.1 | 6.2 | 7 | 6 | 6.2 | 6.2 | 6.2 | 6.3 | 6.1 | 6.2 | 6.5 |
| 7 | 10.31 | 16.77 | 18.89 | 10.3 | 10.4 | 11.7 | 10.2 | 10.4 | 10.5 | 10.7 | 10.5 | 10.3 | 10.4 | 10.7 |
| 8 | 13.8 | 21.54 | 22.69 | 13.9 | 13.5 | 15.3 | 13.6 | 13.7 | 14 | 14 | 14 | 13.8 | 13.9 | 14.2 |
| 9 | 15.45 | 17.32 | 18.27 | 15.5 | 15.6 | 16.5 | 15.2 | 15.4 | 15.6 | 16.1 | 15.5 | 15.4 | 15.5 | 15.7 |
| 10 | 14.86 | 11.26 | 11.01 | 14.5 | 14.9 | 15.2 | 14.7 | 14.8 | 14.9 | 15.3 | 14.8 | 14.9 | 14.8 | 14.9 |
| 11 | 12.73 | 4.87 | 2.85 | 12.7 | 12.7 | 12.2 | 12.7 | 12.7 | 12.7 | 12.8 | 12.6 | 12.7 | 12.7 | 12.5 |
| 12 | 9.25 | 3.25 | 2.04 | 9.2 | 9.2 | 8.2 | 9.4 | 9.3 | 9.3 | 9.1 | 9.1 | 9.3 | 9.2 | 8.8 |
| 13 | 6.14 | 2.16 | 1.36 | 6.1 | 6 | 4.8 | 6.4 | 6.2 | 5.9 | 5.8 | 6 | 6.2 | 6.1 | 5.7 |
| 14 | 3.68 | 1.08 | 0.68 | 3.7 | 3.6 | 2.5 | 3.9 | 3.7 | 3.5 | 3.3 | 3.6 | 3.7 | 3.6 | 3.4 |
| 15 | 1.98 | 0.65 | 0.41 | 2 | 1.9 | 1.2 | 2.2 | 2 | 2 | 1.7 | 1.9 | 2 | 1.9 | 1.8 |
| 16 | 1.01 | 0.43 | 0.27 | 1 | 1 | 0.6 | 1.1 | 1 | 1 | 0.8 | 1 | 1 | 1 | 0.9 |
| 17 | 0.45 | 0.22 | 0.14 | 0.5 | 0.4 | 0.2 | 0.5 | 0.4 | 0.5 | 0.3 | 0.4 | 0.5 | 0.4 | 0.4 |
| Sum | 99.99 | 100 | 100 | 99.7 | 99.7 | 100.3 | 99.9 | 100.1 | 100.2 | 99.9 | 100 | 100.1 | 100 | 100.2 | used in these studies was based on published ranges. The composition used is shown below:

| | |
|---|---|
| KH2PO4 | 2 mM |
| NaCl | 40 mM |
| CaCl2 | 1.5 mM |
| NaOH | to pH 6.2 |

The technique uses a stirred flow-thru cell with a very short residence time. The buccal dissolution test was set up using simulated saliva, with a liquid volume in the cell of 9 ml, and a flow rate of 5.3 ml/min (2.7 ml/min thru the dip tube to waste, and 2.6 ml/min thru the filter and the in-line UV cell). UV cell path length was 1 mm. The tests were run at room temperature Buccal dissolution studies were carried out with neat Formosa benzonatate (abbreviated below as "Benz") and benzonatate resinates prepared from this benzonatate. Preparation of the resinates was at room temperature for 40 hours by the procedure described in Example 2. The reactants and resinate compositions were as shown in Table VI,

TABLE VI

| Resin | Benz, g | Resin, g | Water, g | Benz/Resin ratio | Wt. Fr. Water | Loading, mg/mg | Loading Efficiency, % |
|---|---|---|---|---|---|---|---|
| IRP69H | 0.4977 | 0.5056 | 5.000 | 0.984 | 0.833 | 0.425 | 69.7 |
| IRP64H | 0.5065 | 0.5049 | 5.000 | 1.003 | 0.832 | 0.480 | 87.9 |

Dissolution data were obtained at several benzonatate dosages for both the neat benzonatate and the resinates, and the data were normalized to a dosage of 8 mg. The normalized benzonatate dissolution data are given in Table VII and are plotted as a function of time in FIG. 6. The plot shows the instantaneous concentration of benzonatate released after initial dosage and flow of simulated saliva through the stirred cell.

TABLE VII

Simulated Buccal Dissolution
8 mg dose
5.3 ml/min solvent flow through cell

| | Benzonatate Conc. In Effluent, mg/L | | | Cumulative Benzonatate Released, mg | | |
|---|---|---|---|---|---|---|
| Time (sec) | BENZ | Comp. Ex. 8 IRP69H | Ex. 9 IRP64H | BENZ | Comp. Ex. 8 IRP69H | Ex. 9 IRP64H |
| 0 | 0 | 0 | 0 | | | |
| 5 | 0 | 0 | 0 | | | |
| 10 | 0 | 0 | 0 | | | |
| 15 | 37.3 | 7.0 | 3.3 | 0.008 | 0.002 | 0.001 |
| 20 | 192.8 | 29.6 | 14.0 | 0.059 | 0.010 | 0.005 |
| 25 | 353.0 | 62.9 | 29.0 | 0.180 | 0.030 | 0.014 |
| 30 | 473.4 | 84.1 | 45.0 | 0.362 | 0.062 | 0.030 |
| 35 | 544.2 | 97.7 | 59.0 | 0.587 | 0.103 | 0.053 |
| 40 | 574.7 | 108.2 | 70.1 | 0.834 | 0.148 | 0.082 |
| 45 | 585.5 | 116.3 | 78.3 | 1.090 | 0.198 | 0.115 |
| 50 | 573.6 | 123.0 | 83.8 | 1.346 | 0.251 | 0.150 |
| 55 | 559.0 | 128.8 | 88.1 | 1.596 | 0.306 | 0.188 |
| 60 | 541.7 | 133.4 | 91.0 | 1.839 | 0.364 | 0.228 |
| 65 | 519.6 | 136.9 | 93.3 | 2.074 | 0.424 | 0.269 |
| 70 | 498.0 | 140.3 | 94.6 | 2.298 | 0.485 | 0.310 |
| 75 | 480.4 | 142.7 | 95.6 | 2.514 | 0.547 | 0.352 |
| 80 | 460.2 | 144.7 | 96.6 | 2.722 | 0.611 | 0.395 |
| 85 | 439.9 | 146.4 | 96.6 | 2.921 | 0.675 | 0.437 |
| 90 | 421.8 | 147.3 | 96.6 | 3.111 | 0.740 | 0.480 |
| 95 | 403.2 | 147.6 | 95.9 | 3.293 | 0.805 | 0.522 |
| 100 | 387.3 | 155.1 | 95.3 | 3.468 | 0.872 | 0.565 |
| 105 | 369.4 | 154.8 | 94.6 | 3.635 | 0.940 | 0.607 |
| 110 | 353.5 | 154.0 | 93.0 | 3.795 | 1.009 | 0.648 |
| 115 | 337.8 | 148.8 | 92.0 | 3.947 | 1.075 | 0.689 |
| 120 | 323.0 | 142.7 | 90.7 | 4.093 | 1.140 | 0.729 |
| 125 | 308.9 | 134.5 | 89.4 | 4.233 | 1.201 | 0.769 |
| 130 | 294.9 | 126.1 | 87.7 | 4.366 | 1.259 | 0.808 |
| 135 | 282.2 | 118.9 | 86.1 | 4.494 | 1.313 | 0.846 |
| 140 | 269.8 | 112.8 | 84.5 | 4.615 | 1.364 | 0.884 |
| 145 | 257.6 | 109.0 | 82.9 | 4.732 | 1.413 | 0.921 |
| 150 | 246.0 | 101.8 | 81.2 | 4.843 | 1.459 | 0.957 |
| 155 | 235.2 | 97.4 | 79.6 | 4.949 | 1.503 | 0.993 |
| 160 | 224.7 | 93.7 | 77.6 | 5.051 | 1.546 | 1.028 |
| 165 | 214.7 | 90.2 | 76.0 | 5.148 | 1.586 | 1.061 |
| 170 | 205.2 | 86.4 | 74.4 | 5.241 | 1.625 | 1.095 |
| 175 | 195.8 | 82.9 | 72.7 | 5.329 | 1.663 | 1.127 |
| 180 | 187.1 | 79.7 | 70.8 | 5.414 | 1.699 | 1.159 |
| 185 | 178.8 | 76.6 | 69.2 | 5.495 | 1.733 | 1.190 |
| 190 | 170.9 | 73.7 | 67.5 | 5.572 | 1.766 | 1.220 |
| 195 | 163.1 | 70.8 | 66.2 | 5.646 | 1.798 | 1.249 |
| 200 | 155.8 | 67.9 | 64.6 | 5.716 | 1.829 | 1.278 |
| 205 | 148.8 | 65.2 | 62.6 | 5.783 | 1.858 | 1.306 |
| 210 | 142.0 | 62.6 | 61.3 | 5.848 | 1.886 | 1.334 |
| 215 | 135.6 | 59.7 | 59.7 | 5.909 | 1.913 | 1.361 |
| 220 | 129.6 | 58.0 | 58.4 | 5.967 | 1.939 | 1.387 |
| 225 | 123.7 | 55.7 | 56.8 | 6.023 | 1.965 | 1.412 |
| 230 | 118.3 | 53.6 | 55.5 | 6.077 | 1.989 | 1.437 |
| 235 | 112.9 | 51.9 | 53.8 | 6.128 | 2.012 | 1.461 |
| 240 | 107.8 | 49.9 | 52.5 | 6.177 | 2.034 | 1.484 |
| 245 | 102.9 | 48.1 | 51.2 | 6.223 | 2.056 | 1.507 |
| 250 | 98.3 | 46.4 | 49.9 | 6.268 | 2.077 | 1.530 |
| 255 | 93.7 | 44.7 | 48.6 | 6.310 | 2.097 | 1.551 |
| 260 | 89.7 | 43.2 | 47.3 | 6.350 | 2.116 | 1.573 |
| 265 | 85.6 | 41.5 | 46.3 | 6.389 | 2.135 | 1.593 |
| 270 | 81.8 | 40.3 | 45.0 | 6.426 | 2.153 | 1.613 |
| 275 | 78.0 | 38.9 | 43.7 | 6.461 | 2.171 | 1.633 |
| 280 | 74.5 | 37.7 | 42.7 | 6.495 | 2.188 | 1.652 |
| 285 | 71.3 | 36.2 | 41.8 | 6.527 | 2.204 | 1.671 |
| 290 | 68.1 | 35.1 | 40.8 | 6.558 | 2.220 | 1.689 |
| 295 | 64.8 | 33.9 | 39.5 | 6.587 | 2.235 | 1.707 |
| 300 | 61.6 | 33.1 | 38.5 | 6.615 | 2.250 | 1.724 |

Figure 6:
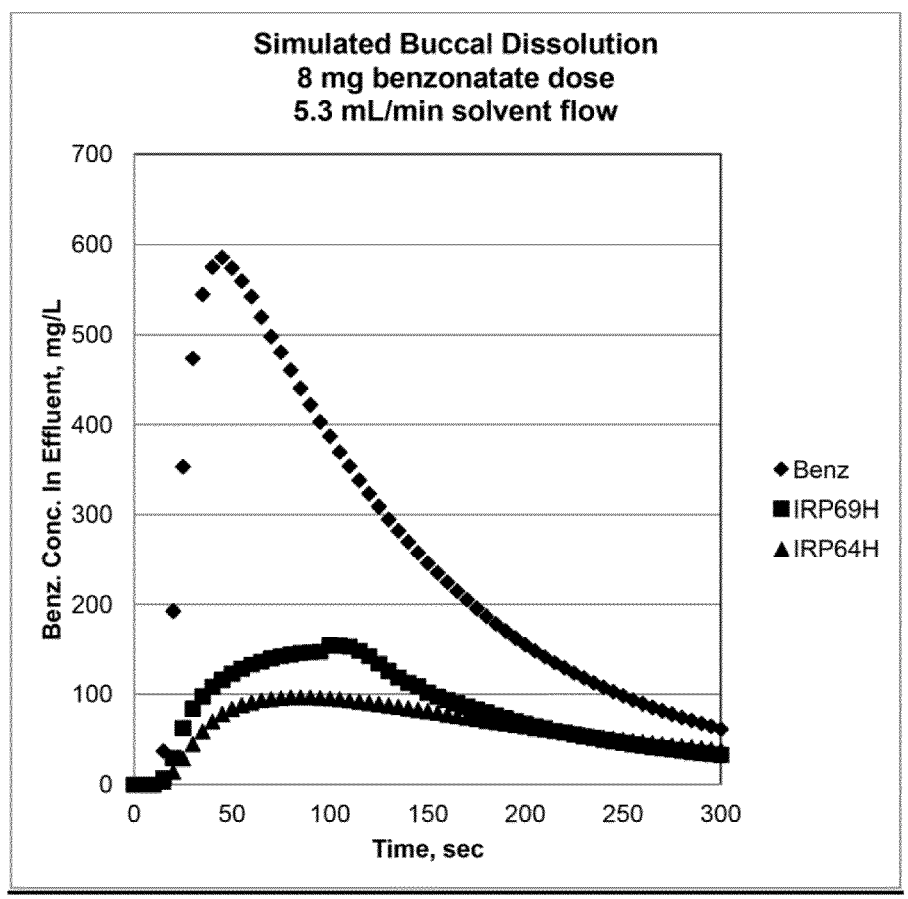
FIG. 6 plots the effluent concentration of benzonatate under simulated buccal dissolution conditions.

As can be seen from Table VII and from FIG. 6, both of the benzonatate resinates showed a large reduction in buccal dissolution as compared to the neat benzonatate. The IRP64H weak acid resinate surprisingly produced a larger reduction in buccal benzonatate release than the IRP69 strong acid resinate. The IRP64H resinate showed a peak concentration of benzonatate less than 20% of the peak concentration from neat benzonatate. Cumulative benzonatate release from the IRP64H resinate was only 12.4% of that of neat benzonatate at the end of 60 seconds, and was only 8.3% of neat benzonatate at the end of 30 seconds.

Accordingly, a benzonatate solid oral dosage form created with an ion exchange resin would lead to a substantial reduction in exposure to benzonatate in the oral cavity and, accordingly, a reduction in the potential choking hazard associated with conventional liquid filled soft gel capsules.

Simulated Gastrointestinal Dissolution Testing

Simulated gastrointestinal dissolution studies were carried out with benzonatate and the resinates shown in Table VI. The dissolution test used procedures devised by DOW Chemical using their proprietary FloVitro™ dissolution apparatus described in U.S. Pat. No. 6,799,123B2 and in the publication titled "FloVitro™ Technology" published online at:
http://www.rohmhaas.com/ionexchange/pharmaceuticals/Formulations doc/FloVitro™ %20Presentation.%202008.pdf.

The disclosures of these documents are herein incorporated by reference to the extent not incompatible herewith.

The system used two different media that were combined during the process. The fluid flow rates were:
Simulated gastric fluid=7.7 ml/min
Simulated intestinal fluid=13.1 ml/mi
Total flow through analyzer=20.8 ml/min
Cell volumes were:
Cell1: 50 ml
Cell 2: 140 ml
Cell 3: 1454 ml
The fluids were:
To Cell 1: USP simulated gastric fluid (no pepsin)
To Cell 2: USP simulated intestinal fluid (pH 6.8) (SIF)
Cell 2 pH: 6.8
Temperature: 37 C
The samples tested were:
a) 100 mg dose neat benzonatate
b) 220.48 mg of IRP69H resinate: 87.97 mg benzonatate dose
c) 225.15 mg of IRP64H resinate: 102.21 mg benzonatate dose a) 100 mg Neat Benzonatate Table VIII below shows the time distribution of homolog concentrations and cumulative release in the effluent of the FloVitro™ apparatus with this dose.

b) Comparative Example 9: 87.97 mg benzonatate dose from IRP 69H resinate

Table IX below shows the time distribution of homolog concentrations and cumulative release in the effluent of the FloVitro™ apparatus with this resinate dose.

c) Example 10: 102.21 mg benzonatate dose from IRP 64H resinate

Table X below shows the time distribution of homolog concentrations in the effluent of the FloVitro™ apparatus with this resinate dose. Table XI below shows the time distribution of the cumulative homolog releases.

Figure 7:
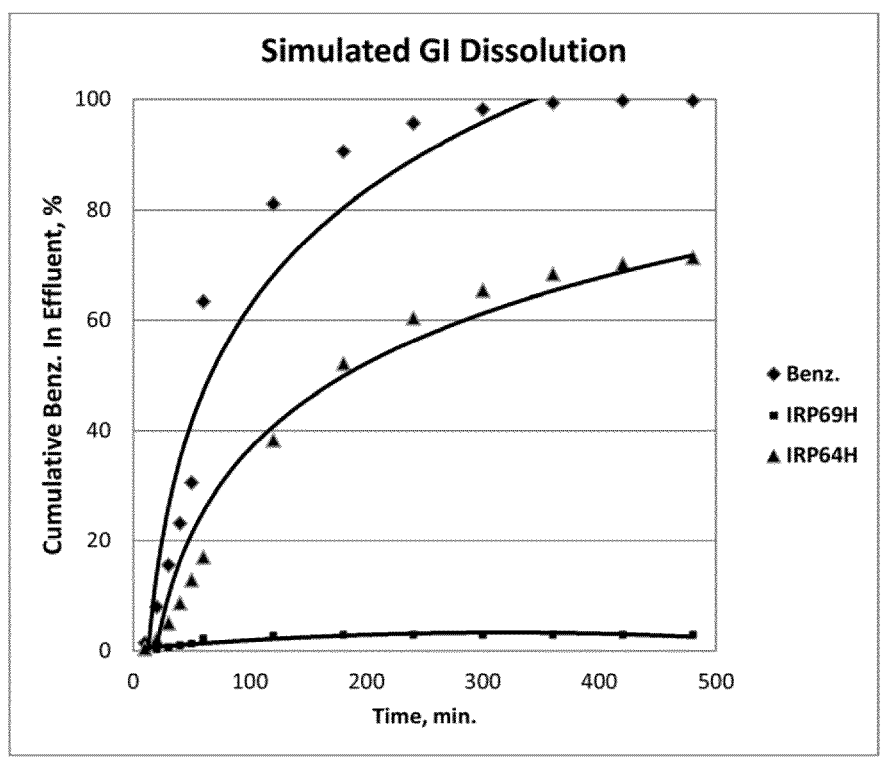
FIG. 7 is a plot of the cumulative benzonatate weight, as a percent of the original dose, in the effluent of simulated gastrointestinal dissolution, as a function of time for neat benzonatate, an IRP69H strong acid resinate and an IRP64H weak acid resinate.

The cumulative releases of benzonatate from neat benzonatate and the resinates of Comparative Example 9 and Example 10 are shown plotted in FIG. 7.

TABLE VIII

Dissolution Profile of 100 mg Neat Benzonatate

Concentration of Homolog in Effluent
Ethoxy Units

| Time, min | $n=3$ mg/L | $n=4$ mg/L | $n=5$ mg/L | $n=6$ mg/L | $n=7$ mg/L | $n=8$ mg/L | $n=9$ mg/L | $n=10$ mg/L | $n=11$ mg/L | $n=12$ mg/L | $n=13$ mg/L | $n=14$ mg/L | $n=15$ mg/L | $n=16$ mg/L | $n=17$ mg/L | Total mg/L | Cumul. mg |
|---|---|---|---|---|---|---|---|---|---|---|---|---|---|---|---|---|---|
| 0 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | |
| 10 | 0.04 | 0.14 | 0.41 | 0.85 | 1.42 | 1.92 | 2.14 | 2.06 | 1.80 | 1.26 | 0.84 | 0.49 | 0.27 | 0.12 | 0.08 | 13.84 | 1.44 |
| 20 | 0.07 | 0.28 | 0.78 | 1.73 | 2.91 | 3.90 | 4.38 | 4.18 | 3.58 | 2.65 | 1.73 | 1.03 | 0.55 | 0.25 | 0.08 | 28.13 | 8.00 |
| 30 | 0.08 | 0.35 | 0.98 | 2.10 | 3.61 | 4.89 | 5.47 | 5.28 | 4.52 | 3.29 | 2.13 | 1.27 | 0.63 | 0.28 | 0.09 | 34.97 | 15.52 |
| 40 | 0.09 | 0.40 | 1.10 | 2.27 | 3.86 | 5.23 | 5.81 | 5.66 | 4.80 | 3.47 | 2.31 | 1.35 | 0.67 | 0.25 | 0.10 | 37.37 | 23.20 |
| 50 | 0.11 | 0.40 | 1.05 | 2.18 | 3.76 | 5.07 | 5.67 | 5.51 | 4.71 | 3.42 | 2.23 | 1.28 | 0.67 | 0.27 | 0.09 | 36.42 | 30.53 |
| 60 | 0.07 | 0.37 | 0.99 | 2.07 | 3.55 | 4.76 | 5.36 | 5.13 | 4.41 | 3.17 | 2.09 | 1.25 | 0.56 | 0.26 | 0.00 | 34.04 | 63.41 |
| 120 | 0.05 | 0.20 | 0.53 | 1.18 | 1.99 | 2.67 | 3.01 | 2.84 | 2.44 | 1.73 | 1.13 | 0.59 | 0.31 | 0.00 | 0.00 | 18.66 | 81.10 |
| 180 | 0.00 | 0.10 | 0.29 | 0.61 | 1.04 | 1.41 | 1.57 | 1.51 | 1.26 | 0.90 | 0.57 | 0.30 | 0.11 | 0.00 | 0.00 | 9.68 | 90.57 |
| 240 | 0.00 | 0.06 | 0.16 | 0.36 | 0.60 | 0.78 | 0.89 | 0.84 | 0.70 | 0.49 | 0.36 | 0.17 | 0.09 | 0.00 | 0.00 | 5.50 | 95.70 |
| 300 | 0.00 | 0.00 | 0.09 | 0.18 | 0.30 | 0.41 | 0.45 | 0.42 | 0.39 | 0.25 | 0.15 | 0.09 | 0.00 | 0.00 | 0.00 | 2.73 | 98.15 |
| 360 | 0.00 | 0.00 | 0.05 | 0.11 | 0.15 | 0.19 | 0.23 | 0.20 | 0.17 | 0.10 | 0.00 | 0.00 | 0.00 | 0.00 | 0.00 | 1.20 | 99.32 |
| 420 | 0.00 | 0.00 | 0.00 | 0.06 | 0.08 | 0.11 | 0.12 | 0.11 | 0.09 | 0.10 | 0.00 | 0.00 | 0.00 | 0.00 | 0.00 | 0.67 | 99.74 |
| 480 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 | |

TABLE IX

Comparative Example 9
Dissolution Profile of 87.97 mg Benzonatate Dose as IRP 69H Resinate Concentration of Homolog in Effluent
Ethoxy Units

| Time, min | $n=5$ mg/L | $n=6$ mg/L | $n=7$ mg/L | $n=8$ mg/L | $n=9$ mg/L | $n=10$ mg/L | $n=11$ mg/L | $n=12$ mg/L | $n=13$ mg/L | $n=14$ mg/L | Total mg/L | Cumul. mg | % Recovery |
|---|---|---|---|---|---|---|---|---|---|---|---|---|---|
| 0 | n.d. | 0.0000 | 0.0000 | 0.0000 | 0.0000 | 0.0000 | 0.0000 | 0.0000 | 0.0000 | 0.0000 | 0.0000 | | |
| 10 | 0.0000 | 0.0000 | 0.0475 | 0.0801 | 0.0806 | 0.0739 | 0.0710 | 0.0434 | 0.0194 | 0.0000 | 0.4159 | 0.043 | 0.05 |
| 20 | 0.0000 | 0.0466 | 0.1002 | 0.0223 | 0.1920 | 0.1897 | 0.1519 | 0.0980 | 0.0565 | 0.0000 | 0.8571 | 0.282 | 0.32 |
| 30 | 0.0000 | 0.0556 | 0.1578 | 0.2374 | 0.2634 | 0.2784 | 0.2319 | 0.1430 | 0.0697 | 0.0000 | 1.4371 | 0.590 | 0.67 |
| 40 | 0.0000 | 0.0801 | 0.1322 | 0.2338 | 0.2893 | 0.2896 | 0.2346 | 0.1501 | 0.0879 | 0.0303 | 1.5278 | 0.905 | 1.03 |
| 50 | 0.0366 | 0.0861 | 0.1463 | 0.2178 | 0.2942 | 0.2822 | 0.2176 | 0.1353 | 0.0868 | 0.0000 | 1.5029 | 1.142 | 1.30 |
| 120 | 0.0000 | 0.0459 | 0.0943 | 0.1156 | 0.1582 | 0.1540 | 0.1315 | 0.0738 | 0.0000 | 0.0000 | 0.7734 | 1.999 | 2.27 |
| 180 | 0.0000 | 0.0258 | 0.0419 | 0.0592 | 0.0871 | 0.0853 | 0.0734 | 0.0305 | 0.0000 | 0.0000 | 0.4033 | 2.413 | 2.74 |
| 240 | 0.0000 | 0.0000 | 0.0312 | 0.0461 | 0.0618 | 0.0495 | 0.0455 | 0.0266 | 0.0000 | 0.0000 | 0.2607 | 2.576 | 2.93 |
| 300 | 0.0000 | 0.0000 | 0.0000 | 0.0000 | 0.0000 | 0.0000 | 0.0000 | 0.0000 | 0.0000 | 0.0000 | 0.0000 | 2.576 | 2.93 |

TABLE IX-continued

Comparative Example 9
Dissolution Profile of 87.97 mg Benzonatate Dose as IRP 69H Resinate Concentration of Homolog in Effluent
Ethoxy Units

| Time, min | n = 5 mg/L | n = 6 mg/L | n = 7 mg/L | n = 8 mg/L | n = 9 mg/L | n = 10 mg/L | n = 11 mg/L | n = 12 mg/L | n = 13 mg/L | n = 14 mg/L | Total mg/L | Cumul. mg | % Recovery |
|---|---|---|---|---|---|---|---|---|---|---|---|---|---|
| 360 | 0.0000 | 0.0000 | 0.0000 | 0.0000 | 0.0000 | 0.0000 | 0.0000 | 0.0000 | 0.0000 | 0.0000 | 0.0000 | | |
| 420 | 0.0000 | 0.0000 | 0.0000 | 0.0000 | 0.0000 | 0.0000 | 0.0000 | 0.0000 | 0.0000 | 0.0000 | 0.0000 | | |
| 480 | 0.0000 | 0.0000 | 0.0000 | 0.0000 | 0.0000 | 0.0000 | 0.0000 | 0.0000 | 0.0000 | 0.0000 | 0.0000 | | |

TABLE X

Example 10
Dissolution Profile of 102.21 mg Benzonatate Dose as IRP 64H Resinate Concentration of Homologs in Effluent
Ethoxy Units

| Time | n = 4 mg/L | n = 5 mg/L | n = 6 mg/L | n = 7 mg/L | n = 8 mg/L | n = 9 mg/L | n = 10 mg/L | n = 11 mg/L | n = 12 mg/L | n = 13 mg/L | n = 14 mg/L | n = 15 mg/L | Total mg/L | Cumul. mg |
|---|---|---|---|---|---|---|---|---|---|---|---|---|---|---|
| 0 | 0.000 | 0.000 | 0.000 | 0.000 | 0.000 | 0.000 | 0.000 | 0.000 | 0.000 | 0.000 | 0.000 | 0.000 | 0.000 | |
| 10 | 0.023 | 0.122 | 0.329 | 0.589 | 0.757 | 0.786 | 0.694 | 0.528 | 0.319 | 0.159 | 0.054 | 0.000 | 4.361 | 0.454 |
| 20 | 0.073 | 0.323 | 0.882 | 1.552 | 2.024 | 2.083 | 1.850 | 1.413 | 0.901 | 0.467 | 0.188 | 0.048 | 11.804 | 2.135 |
| 30 | 0.085 | 0.465 | 1.274 | 2.235 | 2.887 | 3.006 | 2.655 | 2.058 | 1.301 | 0.696 | 0.280 | 0.097 | 17.038 | 5.134 |
| 40 | 0.105 | 0.523 | 1.444 | 2.552 | 3.313 | 3.452 | 3.044 | 2.366 | 1.504 | 0.795 | 0.342 | 0.091 | 19.531 | 8.937 |
| 50 | 0.107 | 0.579 | 1.553 | 2.702 | 3.486 | 3.629 | 3.214 | 2.496 | 1.585 | 0.845 | 0.354 | 0.123 | 20.674 | 13.119 |
| 60 | 0.119 | 0.560 | 1.521 | 2.675 | 3.454 | 3.593 | 3.188 | 2.482 | 1.579 | 0.829 | 0.344 | 0.109 | 20.454 | 17.396 |
| 120 | 0.071 | 0.372 | 1.006 | 1.795 | 2.381 | 2.525 | 2.271 | 1.784 | 1.148 | 0.619 | 0.255 | 0.086 | 14.314 | 39.091 |
| 180 | 0.037 | 0.237 | 0.602 | 1.081 | 1.411 | 1.507 | 1.352 | 1.056 | 0.679 | 0.342 | 0.122 | 0.029 | 8.455 | 53.299 |
| 240 | 0.034 | 0.133 | 0.362 | 0.643 | 0.843 | 0.903 | 0.818 | 0.649 | 0.408 | 0.215 | 0.081 | 0.027 | 5.115 | 61.766 |
| 300 | 0.000 | 0.074 | 0.222 | 0.399 | 0.507 | 0.546 | 0.498 | 0.399 | 0.247 | 0.121 | 0.049 | 0.000 | 3.060 | 66.867 |
| 360 | 0.000 | 0.030 | 0.138 | 0.223 | 0.298 | 0.331 | 0.296 | 0.238 | 0.147 | 0.060 | 0.000 | 0.000 | 1.761 | 69.876 |
| 420 | 0.000 | 0.026 | 0.094 | 0.163 | 0.197 | 0.195 | 0.168 | 0.127 | 0.079 | 0.047 | 0.087 | 0.000 | 1.182 | 71.713 |
| 480 | 0.000 | 0.000 | 0.059 | 0.114 | 0.138 | 0.140 | 0.126 | 0.095 | 0.053 | 0.000 | 0.000 | 0.000 | 0.724 | 72.902 |

TABLE XI

Example 10
Cumulative Dissolution of IRP 64H Resinate by Homolog

Cumulative Release of Homolog
Ethoxy Units

| Time | n = 4 mg | n-5 mg | n-6 mg | n = 7 mg | n = 8 Mg | n = 9 mg | n = 10 mg | n = 11 mg | n = 12 mg | n = 13 mg | n = 14 mg | n = 15 mg | Total mg | % Release |
|---|---|---|---|---|---|---|---|---|---|---|---|---|---|---|
| 0 | | | | 0 | 0 | 0 | 0 | 0 | | | | 0 | | |
| 10 | 0.002 | 0.013 | 0.034 | 0.061 | 0.079 | 0.082 | 0.072 | 0.055 | 0.033 | 0.017 | 0.006 | 0.000 | 0.454 | 0.4 |
| 20 | 0.012 | 0.059 | 0.160 | 0.284 | 0.368 | 0.380 | 0.337 | 0.257 | 0.160 | 0.082 | 0.031 | 0.005 | 2.135 | 2.1 |
| 30 | 0.029 | 0.141 | 0.384 | 0.678 | 0.879 | 0.909 | 0.805 | 0.618 | 0.389 | 0.203 | 0.079 | 0.020 | 5.134 | 5.0 |
| 40 | 0.049 | 0.244 | 0.667 | 1.176 | 1.524 | 1.581 | 1.398 | 1.078 | 0.681 | 0.358 | 0.144 | 0.040 | 8.937 | 8.7 |
| 50 | 0.071 | 0.358 | 0.979 | 1.722 | 2.231 | 2.317 | 2.048 | 1.584 | 1.002 | 0.528 | 0.216 | 0.062 | 13.119 | 12.8 |
| 60 | 0.094 | 0.477 | 1.298 | 2.281 | 2.953 | 3.069 | 2.714 | 2.101 | 1.331 | 0.702 | 0.289 | 0.086 | 17.396 | 17.0 |
| 120 | 0.213 | 1.058 | 2.875 | 5.071 | 6.593 | 6.887 | 6.120 | 4.763 | 3.033 | 1.606 | 0.663 | 0.208 | 39.091 | 38.2 |
| 180 | 0.280 | 1.438 | 3.878 | 6.866 | 8.960 | 9.403 | 8.381 | 6.536 | 4.174 | 2.206 | 0.899 | 0.279 | 53.299 | 52.1 |
| 240 | 0.324 | 1.669 | 4.480 | 7.942 | 10.366 | 10.906 | 9.735 | 7.600 | 4.852 | 2.553 | 1.026 | 0.314 | 61.766 | 60.4 |
| 300 | 0.345 | 1.798 | 4.844 | 8.592 | 11.208 | 11.811 | 10.556 | 8.253 | 5.261 | 2.763 | 1.106 | 0.330 | 66.867 | 65.4 |
| 360 | 0.345 | 1.862 | 5.069 | 8.979 | 11.710 | 12.358 | 11.052 | 8.651 | 5.507 | 2.875 | 1.137 | 0.330 | 69.876 | 68.4 |
| 420 | 0.345 | 1.897 | 5.214 | 9.220 | 12.019 | 12.686 | 11.342 | 8.879 | 5.648 | 2.942 | 1.191 | 0.330 | 71.713 | 70.2 |
| 480 | 0.345 | 1.913 | 5.309 | 9.392 | 12.228 | 12.895 | 11.526 | 9.017 | 5.731 | 2.971 | 1.245 | 0.330 | 72.902 | 71.3 |

As can be seen from Table IX and FIG. 7, the benzonatate release from the IRP69H strong acid resinate in simulated GI dissolution was minimal. The strong acid benzonatate resinate was therefore not useful for therapeutic use. In contrast, the benzonatate release from the IRP64H resinate was in a useful range of about 70% of the release from neat benzonatate.

Figure 8:
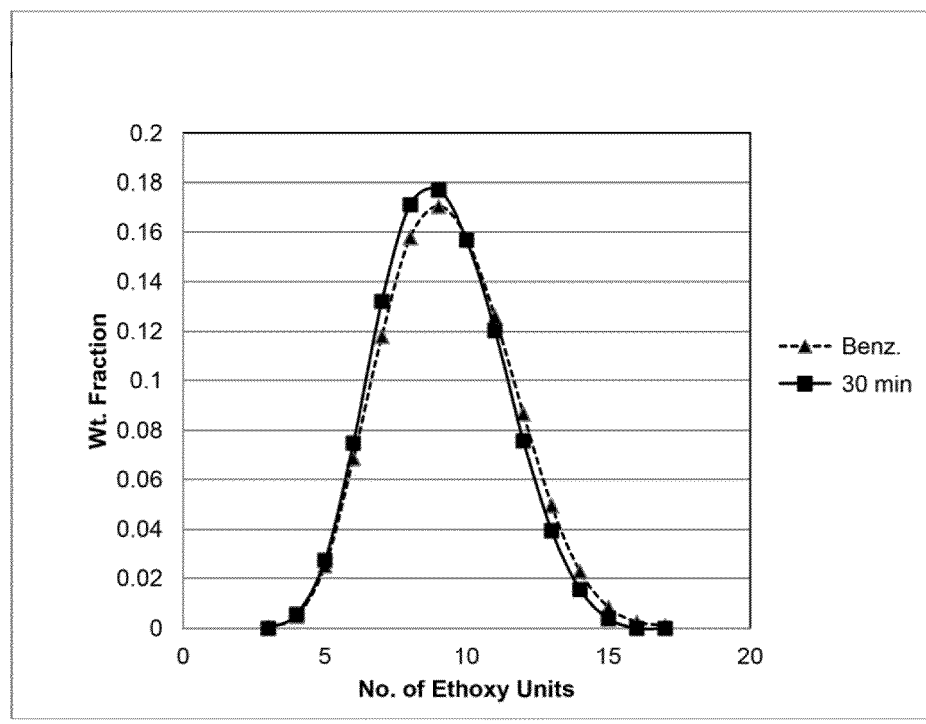
FIG. 8 shows the cumulative homolog distributions in the effluent at 30 minutes of simulated gastrointestinal dissolution for an IRP64H weak acid resinate in comparison with the homolog distribution in TESSALON™ benzonatate.
Figure 9:
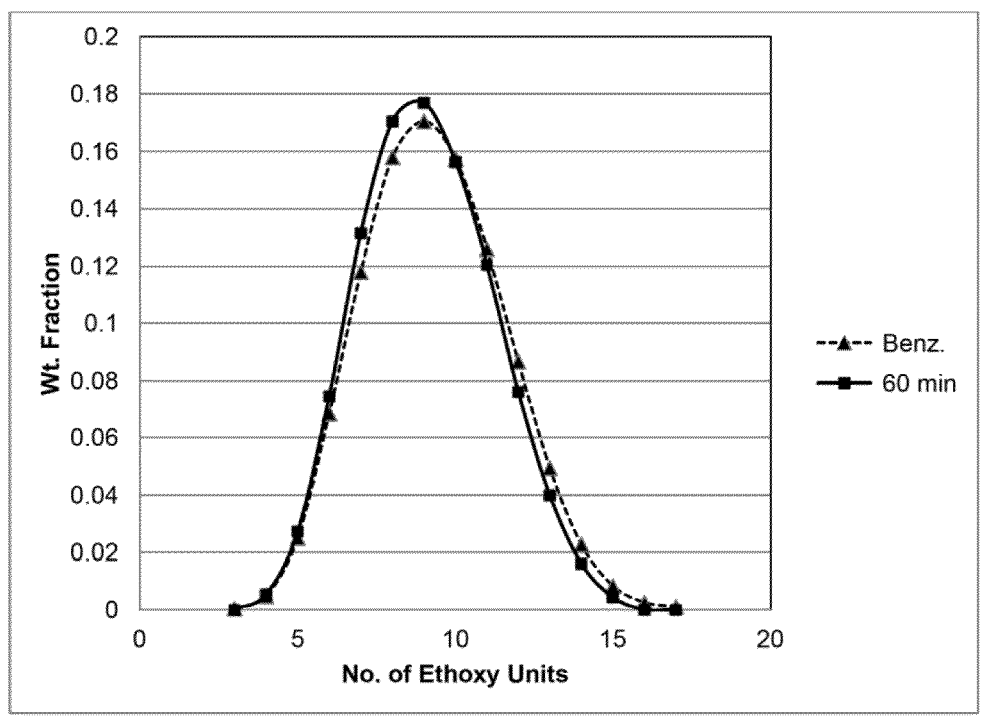
FIG. 9 shows the cumulative homolog distributions in the effluent at 60 minutes of simulated gastrointestinal dissolution for an IRP64H weak acid resinate in comparison with the homolog distribution in TESSALON™ benzonatate.
Figure 10:
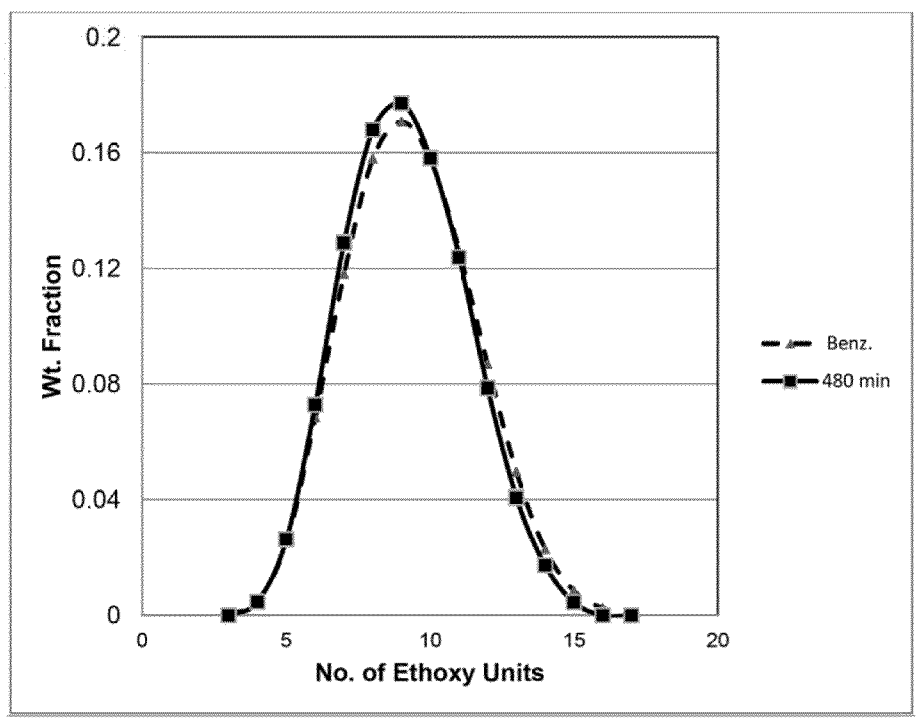
FIG. 10 shows the cumulative homolog distributions in the effluent at 480 minutes of simulated gastrointestinal dissolution for an IRP64H weak acid resinate in comparison with the homolog distribution in TESSALON™ benzonatate.

FIG. 8 shows the cumulative homolog distribution in the effluent after 30 minutes of simulated GI dissolution of the weak acid IRP64H resinate of Example 10 in comparison with the distribution shown in Table III above for the FDA approved benzonatate in TESSALON™. Similarly, FIGS. 9 and 10 show the cumulative homolog distribution in the effluent after 60 minutes and 480 minutes of simulated GI dissolution of the IRP64H resinate of Example 10 in comparison with the distribution inr the FDA approved benzonatate in TESSALON™. Surprisingly, and usefully, the homolog distributions released from the resinate of the invention are in excellent agreement with the homolog distribution in the FDA approved benzonatate for all times.

The distribution of homologs released from the weak acid resinate of the invention was also in excellent agreement with the distribution in the Formosa benzonatate from which it was made. Both of these results are believed novel without counterpart in the prior art Regression analysis of the cumulative weight fractions of homologs in the effluent after 30, 60 and 480 minutes of simulated GI dissolution against the weight fractions shown in Table III for the FDA approved benzonatate in TESSALON™ yielded the statistics shown in Table XII.

TABLE XII

Example 10
Regression of Effluent Distributions Against TESSALON ™ Benzonatate

| Dissolution Time, min | Index of Determination, $R^2$ | Confidence Level | F Ratio |
|---|---|---|---|
| 30 | 0.990 | 2.4E−14 | 1267 |
| 60 | 0.991 | 1.4E−14 | 1377 |
| 480 | 0.994 | 4.5E−16 | 2348 |

The distribution of homologs released from the weak acid resinate of the invention was also in excellent agreement with the distribution in the Formosa benzonatate from which it was made. Regression analysis of the cumulative weight fractions of homologs in the effluent after 30, 60 and 480 minutes of simulated GI dissolution against the weight fractions shown in Table I for the Formosa benzonatate yielded the statistics shown in Table XIII

TABLE XIII

Example 10
Regression of Effluent Distributions Against Formosa Benzonatate

| Dissolution Time, min | Index of Determination, $R^2$ | Confidence Level | F Ratio |
|---|---|---|---|
| 30 | 0.954 | 4.3E−10 | 274 |
| 60 | 0.956 | 3.2E−10 | 285 |
| 480 | 0.965 | 7.8E−11 | 357 |

Both of these results are believed novel without counterpart in the prior art

Comparative Examples 10-18

A series of resination reactions were attempted using the Formosa benzonatate. The reaction conditions varied were as follows:
  the ion-change resin;
    a) a strong acid resin in the salt form consisting of cross-linked sodium polystyrene sulfonate, designated IRP 69
    b) a weak acid resin in the salt form consisting of cross-linked potassium polymethacrylic acid, designated IRP 88
    both resins from Dow Chemical
  the quantity of resin
  the quantity of benzonatate (Wt. Benz)
  the quantity of distilled water
  All the resination reactions were carried out at room temperature overnight.

The reaction procedure was essentially as described in Example 2 except for the variation in the reaction conditions noted above.

The total weight of un-reacted butyl 4-aminobenzoate compounds was measured by UV analysis of the filtrates. The weights of reactants, un-reacted butyl 4-aminobenzoate compounds in the filtrates, and the loading is given tin Table XIV. below.

TABLE XIV

| Comp. Ex. No | Resin | Benz, mg | Resin, mg | Water, g | Benz/Resin ratio | Wt. Fr. Water | Wt. Un-reacted Benz. By UV | Loading, mg/mg |
|---|---|---|---|---|---|---|---|---|
| 10 | none | 20 | 0 | 20 | control | 0.999 | 20.00 | 0 |
| 11 | IRP88 | 20 | 10 | 20 | 2.0 | 0.9985 | 20.08 | 0 |
| 12 | IRP88 | 20 | 25 | 20 | 0.8 | 0.978 | 19.68 | 0.0128 |
| 13 | IRP88 | 20 | 50 | 20 | 0.4 | 0.9965 | 20.02 | 0 |
| 14 | IRP88 | 20 | 100 | 20 | 0.2 | 0.994 | 20.46 | 0 |
| 15 | IRP69 | 20 | 10 | 20 | 2.0 | 0.9985 | 20.12 | 0 |
| 16 | IRP69 | 20 | 25 | 20 | 0.8 | 0.978 | 19.90 | 0.004 |
| 17 | IRP69 | 20 | 50 | 20 | 0.4 | 0.9965 | 20.36 | 0 |
| 18 | IRP69 | 20 | 100 | 20 | 0.2 | 0.994 | 19.80 | 0.01 |

Within the margin of error, no reaction occurred and butyl 4-aminobenzoate resinates were not formed with the salt forms of the strong acid or the weak acid ion-exchange resins.

It has been seen from the above examples that the weak acid resinates the invention are unique in that:
  They possess essentially the same distribution of individual butyl 4-aminobenzoate compounds as the benzonatate from which they were made.
  The weight distribution of 4-aminobenzoate compounds in the resinates are normally distributed with respect to the number of ethoxy units in the homologs.
  Simulated buccal dissolution testing of the resinates shows greatly reduced dissolution compared to neat benzonatate.
  Simulated gastrointestinal dissolution testing of the resinates shows about 70% of the benzonatate release compared to neat benzonatate.
  Simulated gastrointestinal dissolution testing of the resinates shows cumulative homolog release distributions in excellent agreement with the homolog distribution in the benzonatate from which they were made
  Simulated gastrointestinal dissolution testing of the resinates shows cumulative homolog release distributions in excellent agreement with the homolog distribution in the FDA approved benzonatate in TESSALON™.

They differ from strong acid benzonatate resinates in that the latter do not release the benzonatate in useful degree in simulated gastrointestinal dissolution testing.

They are formed from weak acid ion-exchange resins in the acid form and are not formable from a weak acid ion-exchange resin in the salt form.

Although the invention has been described in connection with specific desired embodiments, it should be understood that the invention as claimed should not be unduly limited to such specific embodiments. Various modifications and variations of the described method and system of the invention will be apparent to those skilled in the art without departing from the scope and spirit of the invention. Indeed, various modifications of the described modes for carrying out the invention that are obvious o those skilled in the fields of medicine, immunology, pharmacology, endocrinology, or related fields are intended to be within the scope of the invention.

All publications, patent applications, and patents mentioned in this specification are herein incorporated by reference to the extent not incompatible herewith.

What is claimed is:

1. A resinate composition of matter comprising a mixture of individual butyl 4-aminobenzoate homologs having the formula $C_4H_9$—NH—$C_6H_4$—COO—$(C_2H_4O)_n$—$CH_3$ and the following structure:

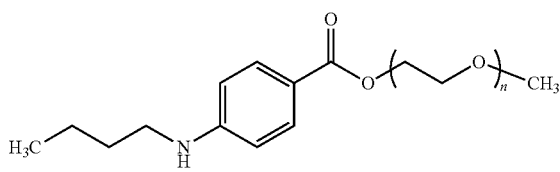

wherein the quantity n is the number of ethoxy units in a butyl 4-aminobenzoate homolog of the mixture, said quantity n having a value in the range of from at least 1 to about 25; and wherein each said homolog is bound to an insoluble, weakly acid, hydrogen form copoly(methacrylic acid-divinybenzene) cation exchange resin in the form of a resinate, said cation exchange resin having the following structure:

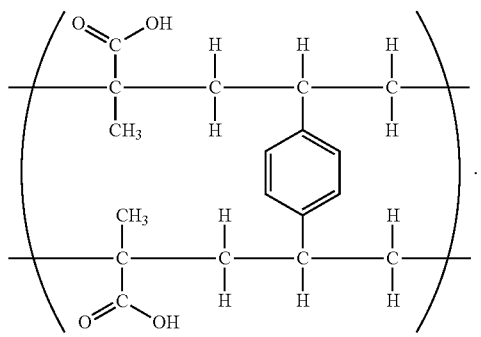

2. The resinate composition of claim 1, wherein the weight fractions of said homologs are normally distributed with respect to the number of ethoxy units in the homologs, a regression of the number of ethoxy units in said homologs against a normal distribution of said weight fractions of the homologs yields an index of determination, $R^2$, of at least about 0.90, a confidence level less than about 0.1, said weight fractions having a peak in the range of from about 6 to about 12 ethoxy units.

3. The resinate composition of claim 1 having the essentially the same distribution of homologs as in the U.S. Food and Drug administration approved prescription drug benzonatate listed in the F.D.A. Orange Book as Application No. N011210, wherein a regression of the weight fractions of the homologs bound in the resinate of claim 1 against the weight fractions of the same homologs in said benzonatate listed in the F.D.A. Orange Book as Application No. N011210, said regression yields an index of determination, $R^2$, of at least about 0.90 and confidence level less than about 0.1.

4. The resinate composition of claim 3, wherein in simulated gastrointestinal dissolution, the distribution of homologs released from the resinate is essentially the same as the homolog distribution in the F.D.A. approved prescription drug benzonatate, said benzonatate listed in the F.D.A. Orange Book as Application No. N011210, the weight fractions of said released homologs, when regressed against the weight fractions of the same homologs in said benzonatate listed in the F.D.A. Orange Book as Application No. N011210, said regression yields an index of determination, $R^2$, of at least about 0.90 and a confidence level less than about 0.1.

5. The resinate composition of claim 1, having essentially the same distribution of homologs as in a mixture of free homologs from which said resinate was made, a regression of the weight fractions of said homologs bound in the resinate against the weight fractions of the same homologs in the mixture of free butyl 4-aminobenzoate homologs from which the resinate composition was made, said regression yields an index of determination, $R^2$, of at least about 0.90 and confidence level less than about 0.1.

6. The resinate composition of claim 5 wherein in simulated gastrointestinal dissolution, the distribution of released homologs is essentially the same as was bound in the resinate, a regression of the released weight fractions against the weight fractions of the same bound homologs, said regression yields an index of determination, $R^2$, of at least about 0.90 and a confidence level less than about 0.1.

7. A resinate composition as in any of claims 2-4 wherein the regression specified in the claim yields an index of determination, $R^2$, at least about 0.94 and a confidence level less than about 0.01.

8. A resinate composition as in any of claims 2-4 wherein the regression specified in the claim yields an index of determination, $R^2$, at least about 0.98 and a confidence level less than about 0.001.

9. A solid oral dosage form pharmaceutical comprising any of the compositions of claims 1 to 4.

10. The solid oral dosage form pharmaceutical as in claim 8 comprising at least one additional pharmaceutical agent.

11. The solid oral dosage form pharmaceutical as in claim 8 comprising at least two pharmaceutical agents bound as resinates to at least one ion exchange resin.

12. The solid oral dosage form pharmaceutical as in claim 9, wherein at least one said resinate is coated with an extended release coating.

13. A solid oral dosage form pharmaceutical comprising any of the compositions of claims 2 to 4 additionally comprising a noxious tasting agent selected from the group consisting of denatonium benzoate, cayenne pepper, capsaicin and their combination.

14. A solid oral dosage form pharmaceutical comprising any of the compositions of claims 2 to 4 comprising at least two pharmaceutical agents bound as resinates to at least one ion exchange resin and additionally comprising a noxious tasting agent selected from the group consisting of denatonium benzoate, cayenne pepper, capsaicin and their combination.

15. A solid oral dosage form pharmaceutical as in claim 9 consisting of a member of the group selected from a tablet, caplet and capsule useful for treatment of cough.

16. A solid oral dosage form comprising any of the compositions of claims 2 to 4 additionally comprising a noxious tasting agent selected from the group consisting of denatonium benzoate, cayenne pepper, capsaicin and their combination, said dosage form being useful for the treatment of cough.

17. A solid oral dosage form pharmaceutical comprising any of the compositions of claims 1 to 4 containing from about 5 to about 1000 mg of butyl 4-aminobenzoate compounds.

18. A solid oral dosage form pharmaceutical comprising a resinate composition of matter comprising a mixture of individual benzonatate homologs having the formula $C_4H_9$—NH—$C_6H_4$—COO—$(C_2H_4O)_n$—$CH_3$ and the following structure:

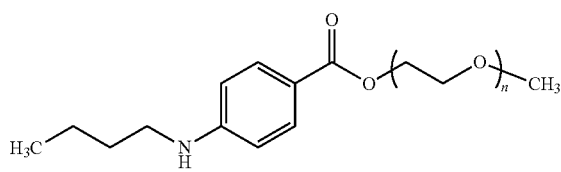

wherein the quantity n is the number of ethoxy units in a benzonatate homolog of the mixture, said quantity n having a value in the range of from at least 1 to about 25; and
wherein each said homolog is bound to an insoluble, weakly acid, hydrogen form copoly(methacrylic acid-divinybenzene) cation exchange resin in the form of a resinate, said cation exchange resin having the following structure:

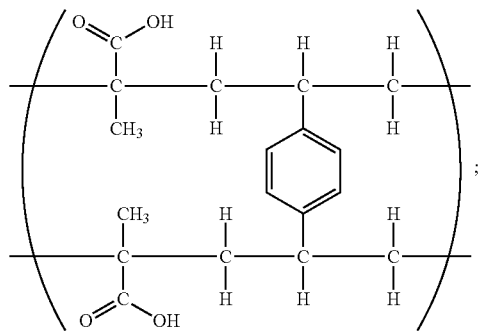

wherein under the same conditions of simulated buccal dissolution, said dosage form shows a lower peak concentration of free benzonatate homologs than a quantity of unbound benzonatate equal to that in said dosage form.

19. The solid oral dosage form as in claim 18,
wherein under the same conditions of simulated buccal dissolution, said dosage form shows a peak concentration of free benzonatate homologs less than about 20 percent of the peak concentration of free benzonatate homologs from a quantity of unbound benzonatate equal to that in said dosage form.

20. A method of treating a patient comprising administrating to a patient in need of benzonatate treatment a solid oral dosage form, said solid dosage form comprising any of the compositions of claims 1 to 4.

21. A method of treating a cough comprising administrating to a patient a solid oral dosage form, said solid dosage form comprising any of the compositions of claims 1 to 4.

22. A method of making a resinate composition as in claim 1, said method comprising the steps:
a) selecting a mixture of individual butyl 4-aminobenzoate compounds having the formula $C_4H_9$—NH—$C_6H_4$—COO—$(C_2H_4O)_n$—$CH_3$, and having the structure shown in FIG. 1; wherein the quantity n in the formula and in FIG. 1 is the number of ethoxy units in a butyl 4-aminobenzoate compound of the mixture, said quantity n having a value in the range of from at least 1 to about 25;
b) selecting an insoluble, weakly acid, hydrogen form cation exchange resin
c) adding said selected mixture of butyl 4-aminobenzoate compounds and the selected weakly acid, hydrogen form cation exchange resin to a sufficient quantity of water to form a slurry wherein the weight ratio of butyl 4-aminobenzoate compounds to cation exchange resin is from about 0.2 to about 1.2 and the weight fraction of water in the slurry is from about 0.5 to about 0.8;
d) reacting said butyl 4-aminobenzoate compounds with said cation exchange resin at a temperature from about 18° C. to about 70° C. for sufficient time to bond said butyl 4-aminobenzoate compounds to said cation exchange resin to form a resinate with a loading efficiency of at least about 70 percent;
e) filtering said resinate from said slurry;
f) rinsing said resinate; and
g) drying said resinate.

23. The method of claim 22 wherein in step a), said selected mixture of butyl 4-aminobenzoate compounds meets the identification and physical test specifications of benzonatate as specified in USP 28.

24. The method of claim 22 wherein for the selected mixture in step a), the weight fractions of butyl 4-aminobenzoate compounds when regressed against the weight fractions of the same compound in the U.S. Food and Drug administration approved prescription drug benzonatate, said benzonatate listed in the F.D.A. Orange Book as Application No. N011210, said regression yields an index of determination, $R^2$, of at least about 0.90 and a confidence level less than about 0.01.

25. The method of claim 24 wherein said regression yields an index of determination, $R^2$, of at least about 0.94 and a confidence level less than about 0.01.

26. The method of claim 24, wherein said regression in step a) yields an index of determination, $R^2$, of at least about 0.98 and a confidence level less than about 0.001.

27. A solid dosage form comprising a resinate composition capable of release of bound butyl 4-aminobenzoate compounds from said resinate in simulated gastrointestinal fluids, wherein the composition of said released compounds is essentially the same as in the U.S. Food and Drug administration approved prescription drug benzonatate, said benzonatate listed in the F.D.A. Orange Book as Application No. N011210, a regression of the cumulative weight fraction of each said released compound against the weight fractions of the same compound in the U.S. Food and Drug administration approved prescription drug benzonatate, said benzonatate listed in the F.D.A. Orange Book as Application No.

N011210, said regression yields an index of determination, $R^2$, of at least about 0.90 and a confidence level less than about 0.1.

28. solid dosage form of claim 27 wherein said regression yields an index of determination, $R^2$, of at least about 0.94 and a confidence level less than about 0.01.

29. The solid dosage form of claim 27 wherein said regression yields an index of determination, $R^2$, of at least about 0.98 and a confidence level less than about 0.001.

* * * * *